(12) United States Patent
Ahmed et al.

(10) Patent No.: US 11,592,422 B2
(45) Date of Patent: Feb. 28, 2023

(54) NANOZYMES WITH RADICAL-SCAVENGING CAPPING AGENTS AND METHODS OF DETECTION THEREWITH

(71) Applicant: EYE3CONCEPTS INC., Burlington (CA)

(72) Inventors: Syed Rahin Ahmed, Hamilton (CA); Greter Amelia Ortega Rodriguez, Hamilton (CA); Satish Kumar Tuteja, Hamilton (CA); Seshasai Srinivasan, Brampton (CA); Amin Reza Rajabzadeh, Burlington (CA)

(73) Assignee: EYE3CONCEPTS INC., Burlington (CA)

( * ) Notice: Subject to any disclaimer, the term of this patent is extended or adjusted under 35 U.S.C. 154(b) by 0 days.

(21) Appl. No.: 17/743,951

(22) Filed: May 13, 2022

(65) Prior Publication Data
US 2022/0268732 A1    Aug. 25, 2022

Related U.S. Application Data

(63) Continuation of application No. PCT/CA2021/050506, filed on Apr. 15, 2021.

(60) Provisional application No. 63/010,471, filed on Apr. 15, 2020.

(51) Int. Cl.
*G01N 27/48* (2006.01)
*C12Q 1/00* (2006.01)
(Continued)

(52) U.S. Cl.
CPC ............. *G01N 27/48* (2013.01); *C12Q 1/001* (2013.01); *C12Q 1/28* (2013.01); *G01N 27/3278* (2013.01); *G01N 33/535* (2013.01)

(58) Field of Classification Search
CPC .. G01N 27/48; G01N 27/3278; G01N 33/535; C12Q 1/001; C12Q 1/28
See application file for complete search history.

(56) References Cited

U.S. PATENT DOCUMENTS 5,873,990 A * 2/1999 Wojciechowski ............................ G01N 33/48714
204/406

OTHER PUBLICATIONS

Wang, Sheng, et al. "Comparison of the peroxidase-like activity of unmodified, amino-modified, and citrate-capped gold nanoparticles." ChemPhysChem 13.5 (2012): 1199-1204. (Year: 2012).*

(Continued)

*Primary Examiner* — Jennifer Wecker
*Assistant Examiner* — Michael Paul Shimek
(74) *Attorney, Agent, or Firm* — Hill & Schumacher

(57) ABSTRACT

Nanozymes capped with a radical-scavenging capping agent are disclosed for use in biosensing assays with improved sensitivity. The radical-scavenging capping agent facilitates the capture and retention of one or more radicals for enhancing a catalytic reaction. In some example embodiments, the nanozyme capped by the radical-scavenging capping agent is capable of catalyzing the decomposition of hydrogen peroxide or molecular oxygen. The capped nanozymes may be incorporated with an electrode, such as the working electrode of an electrochemical sensor, for achieving enhanced catalytic activity and a lower limit of detection. In some example embodiments, the radical-scavenging capping agent is or includes thiocyanate. A rapid ethanol detection device and associated method are described in which the working electrode of an electrochemical sensor is modified by a peroxidase-mimetic nanozyme capped with a radical-scavenging capping agent for the enhanced generation of a reduction current associated with the decomposition of hydrogen peroxide.

27 Claims, 16 Drawing Sheets

(51) Int. Cl.
    *C12Q 1/28* (2006.01)
    *G01N 27/327* (2006.01)
    *G01N 33/535* (2006.01)

(56) References Cited

OTHER PUBLICATIONS

Dominguez, Gustavo A., et al. "Effects of charge and surface ligand properties of nanoparticles on oxidative stress and gene expression within the gut of Daphnia magna." Aquatic toxicology 162 (2015): 1-9. (Year: 2015).*

Fafarman, Aaron T., et al. "Thiocyanate-capped nanocrystal colloids: vibrational reporter of surface chemistry and solution-based route to enhanced coupling in nanocrystal solids." Journal of the American Chemical Society 133.39 (2011): 15753-15761. (Year: 2011).*

Ansar, Siyam M., and Christopher L. Kitchens. "Impact of gold nanoparticle stabilizing ligands on the colloidal catalytic reduction of 4-nitrophenol." ACS Catalysis 6.8 (2016): 5553-5560. (Year: 2016).*

He, Weiwei, et al. "Intrinsic catalytic activity of Au nanoparticles with respect to hydrogen peroxide decomposition and superoxide scavenging." Biomaterials 34.3 (2013): 765-773. (Year: 2013).*

Zhang, Yu, et al. "Point-of-care assay for drunken driving with Pd@Pt core-shell nanoparticles-decorated ploy (vinyl alcohol) aerogel assisted by portable pressure meter." Theranostics 10.11 (Apr. 6, 2020): 5064. (Year: 2020).*

Mu, Jianshuai, et al. "Intrinsic peroxidase-like activity and catalase-like activity of Co 3 O 4 nanoparticles." Chemical Communications 48.19 (2012): 2540-2542. (Year: 2012).*

Lv, F. et al., "A convenient detection system consisting of efficient Au@PtRu nanozymes and alcohol oxidase for highly sensitive alcohol biosensing", Nano. Adv 2, 1583-1589 (2000).

Stasyuka, N. et al., "Amperometric biosensors based on oxidases and PtRu nanoparticles as artificial peroxidase", Food Chem. 285, 213-220 (2019).

Kim, M. et al., J., "A Convenient Alcohol Sensor Using One-Pot Nanocomposite Entrapping Alcohol Oxidase and Magnetic Nanoparticles as Peroxidase Mimetics", Nanoscale and Nanotech 12, 5914-5919 (2012).

Bhamore, J. et al., "Functionalization of gold nanoparticles using guanidine thiocyanate for sensitive and selective visual detection of Cd2+", Sens. and Act. B 334, 129685 (2021).

Lawrence M. et al., "A Simple Method for the Size Controlled Synthesis of Stable Oligomeric Clusters of Gold Nanoparticles under Ambient Conditions", J. Vis. Exp. 108, 1-8 (2016).

Smithies O. et al., "Stable Oligomeric Clusters of Gold Nanoparticles: Preparation, Size Distribution, Derivatization, and Physical and Biological Properties", Langmuir 30, 13394-13404 (2014).

Dawson A. et al., "Complexation of Gold Nanoparticles with Radiolytically Generated Thiocyanate Radicals 2.-)", J. Phys. Chem. B 104, 11842-11846 (2000).

Mah-Heidari, N. et al., "Comparing signal amplification of thiocyanated Gold nanoparticles in the presence of different ions", Int. J. Bio-Inorg. Hybr. Nanomater. 6, 105-111 (2017).

Baschong, W. et al., "Thiocyanate gold": small (2-3 nm) colloidal gold for affinity cytochemical labeling in electron microscopy, Histochem. 83, 409-411 (1985).

Zhang, Y. et al., "Point-of-care assay for drunken driving with Pd@Pt core-shell nanoparticles-decorated ploy(vinyl alcohol) aerogel assisted by portable pressure meter", Theran. 10, 5064-5073 (2020).

Smutok, O. et al., "New micro/nanocomposite with perioxidase-like activity in construction of oxidases-based amperometric biosensors for ethanol and glucose analysis", Anal. Chim. Acta 1143, 201-209 (2021).

Wang, S. et al., "Hollow Prussian Blue nanocubes as peroxidase mimetic and enzyme carriers for colorimetric determination of ethanol", Microchim. Acta 186, 738 (2019).

St. Denis, T. et al., "Thiocyanate potentiates antimicrobial photodynamic therapy: In situ generation of the sulfur trioxide radical anion by singlet oxygen", Free Rad. Bio. and Med. 65, 800-810 (2013).

Eastvold, J., "Hypothiocyanous Acid: An Overview", Free Rad. Bio. and Med. 77, 222 (2005), 11 pages.

Wang, X. et al., "Nanozyme Sensor Arrays for Detecting Versatile Analytes from Small Molecules to Proteins and Cells", Anal. Chem. 90, 11696-11702 (2018).

Sun, Y. et al., "DNA-stabilized bimetallic nanozyme and its application on colorimetric assay of biothiols", Biosens. and Bioelect. 74, 1038-1046 (2015).

Chang, C. C. et al., Enhancement of the Peroxidase-Like Activity of Iodine-Capped Gold Nanoparticles for the Colorimetric Detection of Biothiols, Biosens. 10, 113 (2020).

Lin, J. et al., "Gold alloy-based nanozyme sensor arrays for biothiol detection", Analyst 145, 3916-3921 (2020).

Zhang et al.:, "Point-of-care assay for drunken driving with Pd@Pt core-shell nanoparticles—decorated ploy(vinyl alcohol) aerogel assisted by portable pressure meter", Theranostics, Apr. 6, 2020, vol. 10, pp. 5064-5073, ISSN 1838-7640.

Manea et al., "Nanozymes: gold-nanoparticle-based transphosphorylation catalysts", Angew. Chem. Int. Ed. Engl., Nov. 19, 2004, vol. 43, pp. 6165-6169, ISSN 1433-7851.

Wang et al., "Revealing the intrinsic peroxidase-like catalytic mechanism of heterogeneous single-atom Co—MoS2", Nano-Micro Lett., Nov. 22, 2019, vol. 11, p. 102:1¬102:13 ISSN 2311-6706.

Fafarman et al., "Thiocyanate-capped nanocrystal colloids: vibrational reporter of surface chemistry and solution-based route to enhance coupling in nanocrystal solids", J. Am. Chem. Soc., Oct. 5, 2011, vol. 133, pp. 15753-15761, ISSN 0002-7863.

Alqahtani et al., "Highly sensitive ethanol chemical sensor based on novel Ag-doped mesoporous alpha-Fe2O3 prepared by modified sol-gel process", Nanoscale Res. Lett., May 21, 2018, vol. 13, pp. 157: 4-13, ISSN 1556-276X.

Stankus et al., "Interactions between natural organic matter and gold nanoparticles stabilized with different organic capping agents", Environ. Sci. Technol., Apr. 15, 2011, vol. 45, pp. 3238-3244, ISSN 0013-936X.

Jin, et al., 'Graphene oxide-gold nanozyme for highly sensitive electrochemical detection of hydrogen peroxide', Sensors and Actuators B: Chemical, vol. 274, Aug. 1, 2018, pp. 201-209.

Suherman, et al., 'Electrochemical Hg2+ detection at tannic acid-gold nanoparticle modified electrodes by square wave voltammetry', Analyst, vol. 143, No. 9, Apr. 7, 2018, pp. 2035-2041.

* cited by examiner

| EtOH Added (%) | EtOH found (%) | RSD (%, N=3) | Recovery (%) |
|---|---|---|---|
| 0 | ND | ND | |
| 0.02 | 0.0195 | 2.1 | 97.5 |
| 0.06 | 0.056 | 1.3 | 93.3 |
| 0.14 | 0.143 | 2.7 | 102.14 |
| 0.20 | 0.223 | 2.4 | 111.5 |

NANOZYMES WITH RADICAL-SCAVENGING CAPPING AGENTS AND METHODS OF DETECTION THEREWITH

CROSS-REFERENCE TO RELATED APPLICATION

This application claims priority to U.S. Provisional Patent Application No. 63/010,471, titled "ENHANCED NANOZYMATIC ACTIVITY OF CYANIDE CAPPED GOLD NANOPARTICLES FOR ELECTROCHEMICAL DETECTION OF ETHANOL" and filed on Apr. 15, 2020, the entire contents of which is incorporated herein by reference.

BACKGROUND

While a wide variety of methods currently exist for the detection of alcohol in various sample types, there is currently a need to improve the efficacy and sensitivity of alcohol detection for roadside testing with saliva samples.

Alcohol can be detected in saliva for up to 12-24 hours after consumption. The saliva to blood ratio for alcohol is about 1.10, which makes saliva a good candidate for non-invasive sampling.

Alcohol present in saliva can be oxidized by alcohol dehydrogenase or alcohol oxidase for analytical detection. These enzymatic techniques have been coupled with dyes to obtain colored products for optical or electrochemical detection. Both enzymes have associated advantages and disadvantages.

In contrast to alcohol dehydrogenase, which requires additional NAD+ co-substrate, alcohol oxidase (AOx) is better suited to developing a rapid and field-ready ethyl alcohol (EtOH) sensor, since it facilitates a one-step reaction and is more specific towards EtOH. AOx-based EtOH detection is typically performed as a bi-enzymatic process involving oxidation of EtOH by AOx, which produces hydrogen peroxide ($H_2O_2$), followed by a reduction of the produced $H_2O_2$ by peroxidases. This final $H_2O_2$ reduction step involves the oxidation of colorless dyes to produce a colored product.

Unfortunately, results that rely on the enzymatic activity of natural peroxidase can vary significantly with the alteration of conditions such as temperature, pH, and incubation time. This drawback of natural peroxidase has led to interest in nanozymes as peroxidase mimetics for EtOH detection.

Nanozymes (nanomaterials that work as an enzyme), are a result of advances in nanotechnology and overcome several problems associated with natural enzymes. A variety of nanozymes mimicking oxidase, peroxidase, and catalase have been reported. Peroxidase-mimetic nanozymes have been synthesized and employed to detect vital biomarkers like glucose, lactose, alcohol, and urea. While several peroxidase-mimetic nanozymes been demonstrated, such as those based on using nanoparticles (iron, gold, cobalt, platinum, and ruthenium), nanocomposites, metal organic frameworks, and carbon-based nanomaterials, each of these material systems have associated drawbacks that have hampered their integration into commercial sensing systems.

SUMMARY

Nanozymes capped with a radical-scavenging capping agent are disclosed for use in biosensing assays with improved sensitivity. The radical-scavenging capping agent facilitates the capture and retention of one or more radicals for enhancing a catalytic reaction. In some example embodiments, the nanozyme capped by the radical-scavenging capping agent is capable of catalyzing the decomposition of hydrogen peroxide or molecular oxygen. The capped nanozymes may be incorporated with an electrode, such as the working electrode of an electrochemical sensor, for achieving enhanced catalytic activity and a lower limit of detection. In some example embodiments, the radical-scavenging capping agent is or includes thiocyanate. A rapid ethanol detection device and associated method are described in which the working electrode of an electrochemical sensor is modified by a peroxidase-mimetic nanozyme capped with a radical-scavenging capping agent for the enhanced generation of a reduction current associated with the decomposition of hydrogen peroxide.

Accordingly, in one aspect, there is provided a method of performing an assay to detect an assay signal associated with a presence of hydrogen peroxide, the method comprising:

contacting a solution containing hydrogen peroxide with a capped peroxidase-mimetic nanozyme, the capped peroxidase-mimetic nanozyme comprising a radical-scavenging capping agent;

incubating the solution with the capped peroxidase-mimetic nanozyme such that decomposition of the hydrogen peroxide is catalyzed by the capped peroxidase-mimetic nanozyme; and detecting the assay signal associated with the decomposition of the hydrogen peroxide.

In some example implementations of the method, the radical-scavenging capping agent comprises thiocyanate. In some example implementations of the method, the radical-scavenging capping agent comprises a thiol group. In some example implementations of the method, the radical-scavenging capping agent comprises tannic acid.

In some example implementations of the method, the capped peroxidase-mimetic nanozyme comprises a metallic nanoparticle capped with the radical-scavenging capping agent. The metallic nanoparticle may be selected from the group consisting of gold nanoparticles, silver nanoparticles and copper nanoparticles.

In some example implementations of the method, the solution containing hydrogen peroxide is obtained by contacting an ethanol solution with alcohol oxidase. The assay signal may be processed to infer a concentration of ethanol in the ethanol solution.

In some example implementations, the method further comprises adding a substrate to the solution, the substrate being selected to exhibit a color change upon oxidation of the substrate by the hydrogen peroxide in the presence of the capped peroxidase-mimetic nanozyme; wherein the assay signal is a colorimetric assay signal. The substrate may be 3,3',5,5'-tetramethylbenzidine.

In some example implementations of the method, the capped peroxidase-mimetic nanozyme resides on an electrode and wherein the assay signal is a voltametric assay signal. The voltametric assay signal may be associated with the reduction of the hydrogen peroxide by the electrode, and the reduction may be catalyzed by the capped peroxidase-mimetic nanozyme. The method may further comprise adding a substrate to the solution, the substrate being oxidizable by the hydrogen peroxide in the presence of the capped peroxidase-mimetic nanozyme; wherein the assay signal is a reduction current associated with reduction of the oxidized substrate by the electrode.

In some example implementations of the method, the radical-scavenging capping agent comprises thiocyanate, and the solution containing hydrogen peroxide is obtained by contacting an ethanol solution with alcohol oxidase, and wherein the assay signal is processed to infer a concentration of ethanol in the ethanol solution.

The method may further include adding a substrate to the solution, the substrate being selected to exhibit a color change upon oxidation of the substrate by the hydrogen peroxide in the presence of the capped peroxidase-mimetic nanozyme; wherein the assay signal is a colorimetric assay signal. The substrate may be 3,3',5,5'-tetramethylbenzidine. The capped peroxidase-mimetic nanozyme may reside on an electrode and wherein the assay signal is a voltametric assay signal. The voltametric assay signal may be associated with the reduction of the hydrogen peroxide by the electrode, and the reduction may be catalyzed by the capped peroxidase-mimetic nanozyme. The solution may be incubated for less than 5 minutes, 3 minutes, 2 minutes, or less that or equal to 1 minute before reading the assay signal. The concentration of ethanol inferred from the assay signal may be between 0.1% and 0.02%. The method may further include adding a substrate to the solution, the substrate being oxidizable by the hydrogen peroxide in the presence of the capped peroxidase-mimetic nanozyme; wherein the assay signal is a reduction current associated with reduction of the oxidized substrate by the electrode. The substrate may be 3,3',5,5'-tetramethylbenzidine.

In another aspect, there is provided an electrochemical sensor for detecting a presence of ethanol in a sample, the electrochemical sensor comprising a working electrode modified with a capped peroxidase-mimetic nanozyme, wherein the capped peroxidase-mimetic nanozyme comprises a radical-scavenging capping agent. The electrochemical sensor may further include control and processing circuitry operatively coupled to the working electrode, the control and processing circuitry comprising at least one processor and associated memory, the memory being programmed with instructions executable by the at least one processor for performing operations comprising: performing a voltametric scan to obtain an assay signal associated with reduction of a hydrogen peroxide at the working electrode, the reduction being catalyzed by the capped peroxidase-mimetic nanozyme; and processing the assay signal to infer a concentration of ethanol in according to calibration data stored in the memory.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 1A illustrates the colorimetric detection of EtOH, FIG. 1B illustrates the electrochemical detection of EtOH based on reduction current of oxTMB, and FIG. 1C illustrates the electrochemical detection of EtOH based on reduction current of $H_2O_2$.

FIG. 3B shows a far view TEM image of TC-Au NPs.

FIG. 3D is a TEM image of Chi-Au NPs and FIG. 3E plots the absorbance spectra color developed due to nanozymatic activity of NPs (inset: the color of solution).

(FIG. 4B) reaction times (reaction conditions: 5-mM TMB, 10-mM $H_2O_2$ and pH 7.5 at 25° C.); (FIG. 4C) various $H_2O_2$ concentrations with a fixed TMB concentration of 5 mM; and (FIG. 4D) various TMB concentrations with a fixed $H_2O_2$ concentration of 10 mM. The reaction conditions were fixed at pH 7.5 and 25° C. The error bars denote the standard deviation (n=3).

(FIGS. 5A and 5C) 5 mM TMB and different-concentration $H_2O_2$, (FIGS. 5B and 5D) 10 mM $H_2O_2$ and different-concentration TMB.

(FIG. 10A) CV of EtOH detection using reduction current of TMB within 1 min; (FIG. 10B) CV of EtOH detection using reduction current of TMB within 2 min; (FIG. 10C) CV of EtOH detection using reduction current of TMB within 3 min; (FIG. 10D) CV of EtOH detection using reduction current of TMB within 4 min; (FIG. 10E) CV of EtOH detection using reduction current of TMB within 5 min & (FIG. 10F) calibration curve of current vs EtOH at different concentration and time.

(FIG. 11A) CV of bare PBS buffer; (FIG. 11B) CV of PBS buffer and AOx; (FIG. 11C) CV of PBS buffer, AOx, and TC-Au NPs; and (FIG. 11D) CV of PBS buffer, AOx, TC-Au NPs, and $H_2O_2$.

DETAILED DESCRIPTION

Figure 1A:
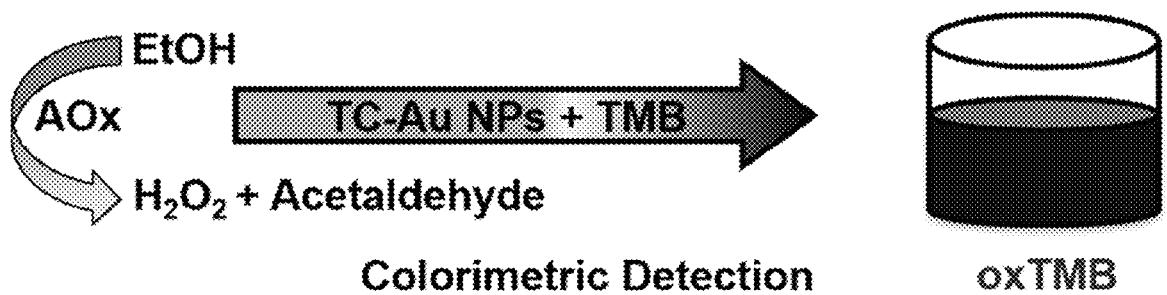
FIGS. 1A-1C illustrate three example methods of EtOH detection, where

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

The present inventors, recognizing the limitations of existing peroxidase-mimetic nanozymes, sought to develop improved peroxidase-mimetic nanozymes that would address that would be readily manufacturable and suitable for integration into a commercial biosensing platform involving peroxide detection. In particular, the present inventors identified the need to provide peroxidase-mimetic nanozymes that would be (i) simple to manufacture, (ii) inexpensive, (iii) stable for extended time periods, (iv) compatible with electrochemical detection, and (v) facilitate the fabrication of a portable ethanol (EtOH) detection platform with a readout time of less than 5 minutes.

The present inventors reasoned that these needs could potentially be met by ligands which, when employed to cap a peroxidase nanozyme, that is, a nanomaterial having peroxidase-mimetic properties, would lead to an enhancement of the peroxidase-mimetic properties. The present inventors realized that, since the catalytic breakdown of peroxide involves the generation of hydroxyl ions, the addition of capping materials capable of scavenging hydroxyl radicals and retaining could potentially lead to an enhancement of catalytic activity by a nanozyme.

Accordingly, in various aspects of the present disclosure, improved nanozymes are provided that include a nanozyme (a nanomaterial exhibiting catalytic activity) capped with a radical-scavenging capping agent (a material capable of acting as nanomaterial capping agent that facilitates the capture and retention of one or more radicals). In some example embodiments, the nanomaterial that is capped by the radical-scavenging capping agent may be any nanozyme that is capable of catalyzing a redox reaction. In some example embodiments, the nanomaterial that is capped by the radical-scavenging capping agent may be any peroxidase-mimetic nanozyme (or oxidase-mimic, superoxide dismutase mimics or catalase mimic) that is capable of catalyzing the decomposition of hydrogen peroxide or oxygen molecule.

As explained in the examples below, the present inventors found that thiocyanate, which is capable of scavenging hydroxyl radicals, to be effective in improving the activity of peroxidase-mimetic nanozymes when employed as a capping agent. The present inventors demonstrated this improved peroxidase-mimetic activity of thiocyanate-capped nanozymes in the non-limiting example cases of (i) the colorimetric detection of ethanol (EtOH) via hydrogen peroxide decomposition and oxidation of TMB (3,3',5,5'-Tetramethylbenzidine), (ii) the electrochemical detection of EtOH via hydrogen peroxide decomposition and the direct measurement of the reduction current of $H_2O_2$, and (iii) the electrochemical detection of EtOH via hydrogen peroxide decomposition, TMB oxidation, and the electrochemical detection of the reduction current of oxidized TMB. In the present examples, the nanozymes employed were gold nanoparticles, although as described below, a wide variety of nanozymes may be capped and employed to catalyze reactions for biosensing.

Figure 1B:
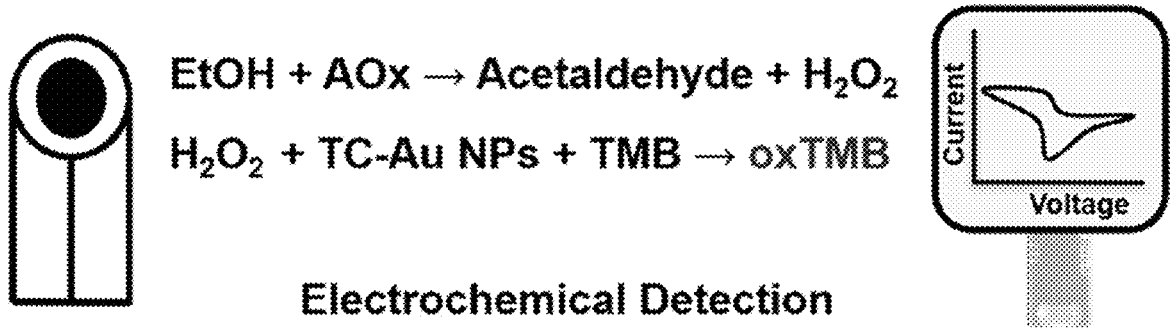
Figure 1C:
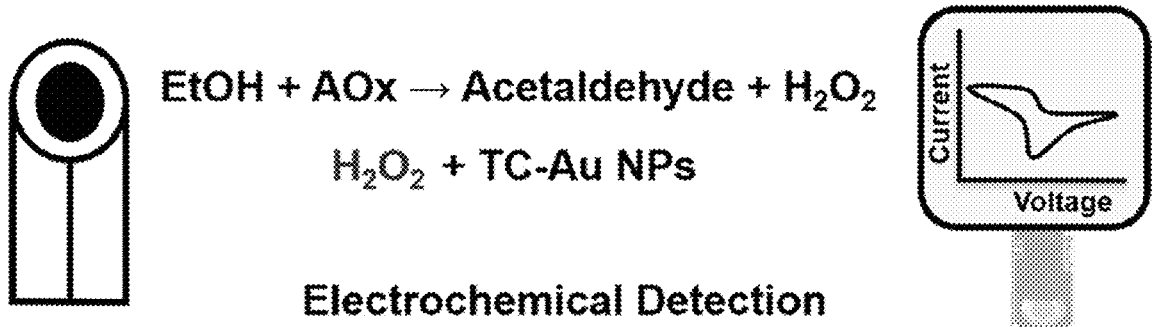

These three example cases are illustrated in FIGS. 1A-1C, respectively. In all examples, alcohol oxidase (AOx) is employed to initially generate $H_2O_2$ from EtOH and the thiocyanate-capped gold nanoparticles, henceforth referred to as TC-Au NPs, are employed to catalyze the decomposition of $H_2O_2$. In FIG. 1A, the TC-Au NPs catalyze the decomposition of $H_2O_2$, which subsequently oxidizes TMB, leading to a detectable colorimetric change. In FIG. 1B, the TC-Au NPs catalyze the decomposition of $H_2O_2$, which subsequently oxidizes TMB, and the oxidized TMB is reduced at the working electrode of an electrochemical sensor and generates a measurable reduction current, as shown in the current-voltage (CV) curve. In FIG. 10, the TC-Au NPs catalyze the decomposition of $H_2O_2$ at the working electrode of an electrochemical sensor, and the resulting reduction current is measured.

Without intending to be limited to theory, it is believed that in each case, the thiocyanate capping (thiocyanate ligand) facilitates the retention of hydroxyl radicals that are generated via the decomposition of $H_2O_2$, as catalyzed via the nanozyme. This retention of the radicals, in turn, leads to an enhancement of the overall nanozymatic activity of the capped nanozyme. This interpretation is consistent with experimental results that are presented below and demonstrate the generation of hydroxyl ions from $H_2O_2$ in the presence of the thiocyanate cap and the increased nanozymatic oxidation of TMB in the presence of the thiocyanate cap.

Figure 1D:
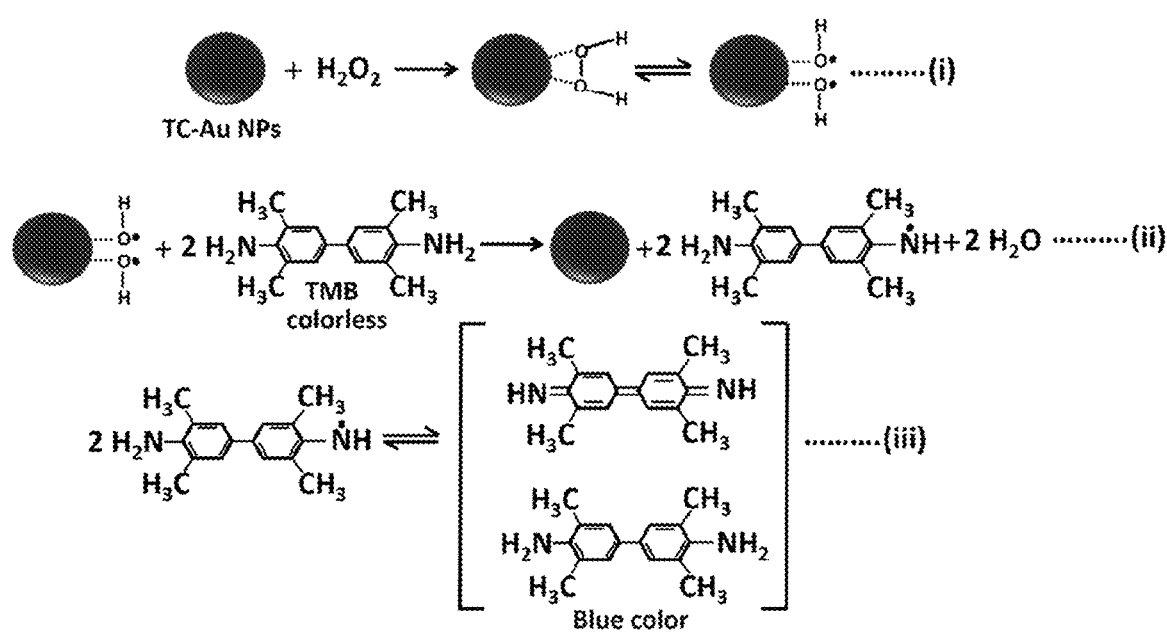
FIG. 1D illustrates the mechanism of TC-Au NPs nanozymatic activity for in colorimetric reactions employed TMB, presented schematically as the following reactions: (i) the formation of .OH radicals through breaking of $H_2O_2$ on TC-Au NPs surface; (ii) .OH radicals initiate the oxidization of TMB; and (iii) the formation of a blue-colored solution.

FIG. 1D schematically illustrates a potential nanozymatic mechanism associated with the TC-Au NPs in the example case of FIG. 1A. It reaction (i), the enzymatically-generated $H_2O_2$ is adsorbed onto the surface of TC-Au NPs and broken down to generate .OH radicals. As shown in the later steps of reaction (i), the thiocyanate cap, which functions as an .OH radical scavenger, facilitates the retention (holding) of the radicals on the TC-Au NPs surface. As shown in reaction (ii), the retained hydroxyl ions facilitate the oxidation of TMB molecules that adsorb onto the surface of the TC-Au NPs and react with the surface .OH radicals. In step (iii), the oxidized TMB yields products that cause the solution to exhibit a blue color, thereby facilitating colorimetric detection. As the TC-Au capping agent supports .OH radicals on the nanoparticle surface, a greater amount of TMB is oxidized and the intensity of the color will be stronger than that which would be achievable in the absence of the TC capping agent.

While many of the examples described herein relate to the use of thiocyanate as a capping agent for increasing the activity of a nanozyme, it will be understood that a wide variety of radical-scavenging capping agents may be employed. For example, in some implementations, the capping agent may be a ligand having a thiol group, such as, but not limited to, cysteine, penicillamine, thiol-poly-L-lysine-thiol, thiol-PEG-amine hydrochloride, and glutathione. In other example implementations, radical-scavenging capping agents that are absent of thiol functional groups may be employed, such as, but not limited to, tannic acid.

In some example implementations, a mixture of capping agents may be employed to provide a radical-scavenging cap on a nanozyme to provide enhanced nanozymatic activity. In some example implementations, a collection capped nanozymes may be provided such that one subset of the capped nanozymes are capped with a first radical-scavenging capping agent and a second subset of the capped nanozymes are capped with a second radical-scavenging capping agent.

While many of the examples described herein relate to the use of gold nanoparticles as nanozymes that are capped by a radical-scavenging capping agent, it will be understood that a wide variety of nanomaterials may be employed and capped by a radical-scavenging capping agent. Non-limiting examples of suitable nanomaterials include, but are not limited to, nanoparticles, nanocrystals, nanospheres, nanotubes, nanodots, nanofibers, nanofibrils, quantum dots, nanoplatelets.

In some example implementations, the nanozyme that is capped with the radical-scavenging capping agent is a metallic nanoparticle. Non-limiting examples of nanozymatic metallic nanoparticles include iron (Fe), gold (Au), cobalt (Co), platinum (Pt), ruthenium (Ru) nanoparticles. In other examples, a nanozyme may be a nanocomposite having catalytic properties, such as a metalorganic framework. In other example implementations, the nanozyme may be a carbon-based nanomaterials having catalytic properties.

While many of the nanozymes disclosed herein are peroxidase mimetics, it will be understood that nanozymes exhibiting other types of catalytic properties may be employed and capped by a radical-scavenging capping agent.

Methods of Preparation of Radical-Scavenging Capped Nanozymes

In some example implementations, radical-scavenging capped nanozymes can be generated according to a one-step method. For example, in the case of thiocyanate-capped metallic nanoparticles, an aqueous solution of a metal precursor (such as, for example, chloroauric acid, silver nitrate or copper nitrate) is heated and combined with a solution of an aqueous thiocyanate salt, such as an aqueous sodium thiocyanate solution. The resulting solution is heated until the formation of thiocyanate capped nanomaterials is signaled by a change in the color (reddish pink) of the solution. The resulting suspension of synthesized thiocyanate capped nanomaterials may be further processed (e.g. via centrifugation or filtration) to separate the radical-scavenging capped nanozymes.

Thiocyanate-capped metallic nanoparticles can be synthesized through delay time method, for example, a mixture of borax and chloroauric acid is stirred vigorously; after a chosen time (1 second to several hours) sodium thiocyanate was added rapidly with brief vigorous mixing. The resulting mix was kept overnight to ensure completion of the reduction.

The reduction of chloroauric acid using sodium thiocyanate in presence of potassium carbonate may also be employed, in which an initial yellow color of solution becomes reddish brown after several days indicates the formation of thiocyanate-capped gold nanoparticles.

Detection of Analytes Via Assays Employing Radical-Scavenging Capped Nanozymes

In some example implementations, the radical-scavenging capped nanozymes disclosed herein are employed for biosensing applications. While the present examples disclose the use of radical-scavenging capped nanozymes for colorimetric assays and electrochemical assays, it will be understood that radical-scavenging capped nanozymes may be employed for a wide variety of enzymatic assay formats, including, but not limited to, solid phase heterogenous assays, homogenous assays, fluorescence assays, chemiluminescent assays, colorimetric assays, agglutination (e.g. light scattering) assays, and electrical-based assays, as described in further detail below. The radical-scavenging capped nanozymes may reside in a suspension during the assay or may reside in contact with a solid phase, such as an electrode.

In some example implementations, the assay may involve the detection of an assay signal associated with an oxidized substrate. For example, the substrate may be oxidized in the presence of hydrogen peroxide and a peroxidase mimetic radical-scavenging capped nanozyme. Non-limiting examples of suitable substrates include TMB, di-azo-aminobenzene (DAB) and o-phenylenediamine (OPD).

Furthermore, it will be understood that the radical-scavenging capped nanozymes may be employed in a wide variety of assay platforms, including reagent kits for performing bench-level assays and assay cartridges or other consumables for use with an assay device. In some example implementations, radical-scavenging capped nanozymes may be integrated within a microfluidic assay device. Non-limiting examples of assay devices are described in further detail below.

While some example assay implementations may involve the detection of a substrate that is oxidized or reduced in the presence of the radical-scavenging capped nanozymes, other example assays may involve the competitive detection of one or more other enzymes (natural or synthetic) that compete for a common substrate. Another radical-scavenging capped nanozymes based assay may involve the colorimetric (fluorescence or electrochemical) "on-off" method where the presence of target may enhance the color, fluorescence or electrical signal or may decrease the intensity of color, fluorescence of electric current.

In some example implementations, the radical-scavenging capped nanozymes exhibit peroxidase-mimetic behavior and are employed for biosensing assays that involve the generation and/or detection of hydrogen peroxide. Non-limiting examples of such assays include ethanol assays, glucose detection, lactic acid detection, urea detection, assays for the generation of, consumption of, and/or use in signaling of hydrogen peroxide in cellular and metabolic processes, detection of cancer, detection of neurodegenerative diseases, detection of inflammatory conditions, in-vivo fluorescent imaging, studies of oxidative microenvironments in cells.

In some example applications, radical-scavenging capped nanozymes can be functionalized with recognition elements for the selective detection of one or more analytes and a separation step can be performed, such that the functionalized radical-scavenging capped nanozymes are retained or removed based on the presence or absence of the analyte, such that the subsequent performing of an assay based on the catalytic action of the remaining radical-scavenging capped nanozymes on a suitable substrate can provide a signal dependent on the presence of the analyte.

For example, a viral-specific antibody (or other suitable recognition element, such as an aptamer or a molecularly-imprinted polymer) may be tagged (conjugated) to a radical-scavenging capped nanozyme. A sample containing the viral particles may be contacted with a solid phase that is configured to be adherent (specifically or non-specifically) to the viral particles. The functionalized radical-scavenging capped nanozymes may then be contacted with the viral particles captured on the solid phase, where they are retained via specific interactions between the antibodies and the viral particles. After performing one or more washing steps, a substrate, such as TMB-$H_2O_2$, may be added and the presence of the viral particles may be detected (and optionally quantified) by detection of a signal (e.g. a color) associated with the decomposition of the substrate.

In some example implementations, radical-scavenging capped nanozymes are employed in assays involving electrical detection, such as, but not limited to, electrochemical assays. In such cases, the radical-scavenging capped nanozymes may be deposited onto a working (or sensing) electrode to form a modified electrode. Non-limiting examples of suitable electrical detection assay modalities include electrochemical detection modalities including voltametric sensors, potentiometric sensors, amperometric sensors, and other examples include field-effect-transistor-based sensors, chemiresistive sensors and conductometric sensors.

It will be understood that the present example assays may be implemented to detect analytes in a wide range of sample types. The sample can be a biological sample which can be, without limitation, an ex vivo bodily fluid that can be a non-invasively obtained fluid (saliva, sputum, urine, tears, etc.) or invasively obtained (blood, plasma, cerebral spinal fluid, etc.). In an embodiment, the bodily fluid is an oral fluid. The oral fluid can include saliva, sputum, or a combination thereof. The sample can be used with the sensor described herein without being processed (e.g., an unprocessed sample). In some embodiments, the bodily fluid sample can first be processed before being used with the sensor described herein.

Example Electrochemical Detection Devices

In various example embodiments, improved electrochemical detection devices are provided by having a working electrode that is modified by the presence of radical-scavenging capped nanozymes. As described above, the presence of the radical-scavenging capped nanozymes can facilitate an enhanced electrochemical response via the trapping, in close proximity to the electrode surface, radicals generated via reactions catalyzed by the nanozyme.

Figure 2A:
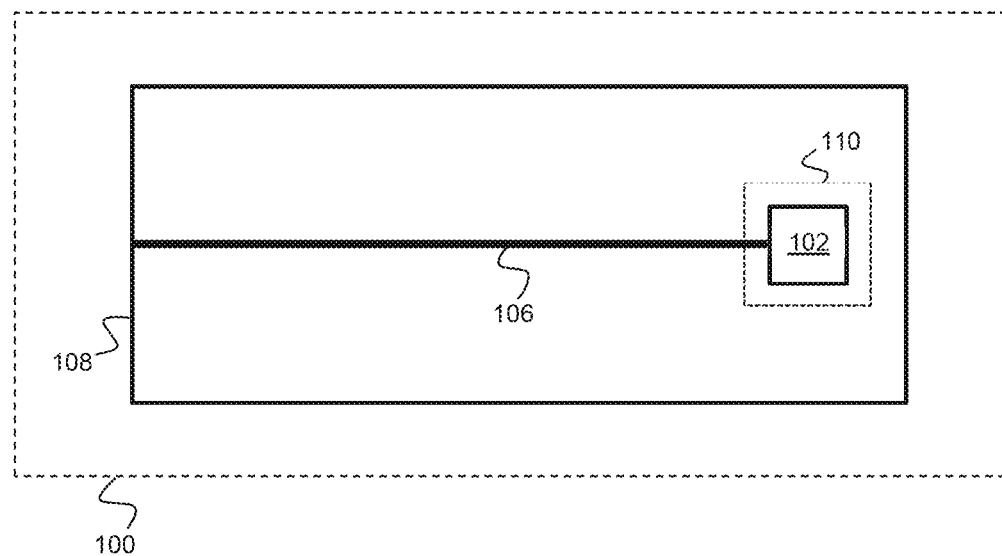
FIGS. 2A and 2B illustrate example sensor configurations for performing electrochemical detection of phenolic analytes using a modified electrode.

An example embodiment of a sensing device 100 including a modified electrode 102 is shown in FIG. 2A. The modified electrode 102 may be a working electrode of an electrochemical sensor. In the embodiment presented in this figure, the modified electrode 102 has been modified to include one or more layers of radical-scavenging capped nanozymes. The modified electrode 102 can be provided on a substrate 108. The substrate 108 can be an insulated substrate. It is possible that the modified electrode 102 be self-supporting and as such the substrate 108 may be omitted. A connection 106 connects the modified electrode 102 to the edge of the substrate 108 or to a contact surface or connecting pad (not shown in the figure). In the sensor 100 shown in FIG. 2A, a sample receiving region 110 is in fluid communication with the modified electrode 102. For example, the sample region 110 may be defined to allow contact between the sample and the sensing electrode 102. It will be understood that the sample receiving region 110 does not need to cover the modified electrode 102, in part or in whole (as shown in FIG. 2A), as other configurations for providing fluid communication between the sample receiving region 110 and the sensing electrode 102 can be used (a microfluidic channel for example).

In some example implementations, an electrochemical sensing device may include multiple modified working electrodes. The multiple working electrodes may have the same modified working electrode structure (e.g. for performing multiple tests in parallel) or may have one or more different modified electrodes, where at least two of the modified electrodes may be configured to catalyze different electrochemical reactions.

In some example implementations, the sensor includes one or more reference electrodes. A reference electrode may be associated with one or more working electrodes of a sensing device. The reference electrode is an electrode with a stable and well-defined electrochemical potential against which the potential of the working electrode(s) can be controlled and measured. When the reference electrode is in use, it is intended to be covered by the sample. In one embodiment, the reference electrode comprises or consists of silver. In some example implementations involving a screen printed reference electrode, the reference electrodes maybe prepared with Ag/AgCl ink or Ag ink.

In some example embodiments, the sensor includes one or more counter electrodes. In an embodiment, each working electrode can be associated with one counter electrode. In another embodiment, two or more working electrodes can be associated with the same counter electrode. The counter electrode completes the circuit of a three-electrode cell, as it allows the passage of current. After the sample is placed on a sample receiving region, a potential is applied between the working electrode and the reference electrode, and the current induced is measured. At the same time, a potential between the counter electrode and the reference electrode is induced which will generate the same amount of current (reverse current). Therefore the working electrode, reference electrode, and counter electrode are all intended to be in fluid communication with the sample. The counter electrode can be made of the same materials as the working electrode and/or the reference electrode. In one example, the counter electrode comprises or consists of carbon ink or platinum.

Figure 2B:
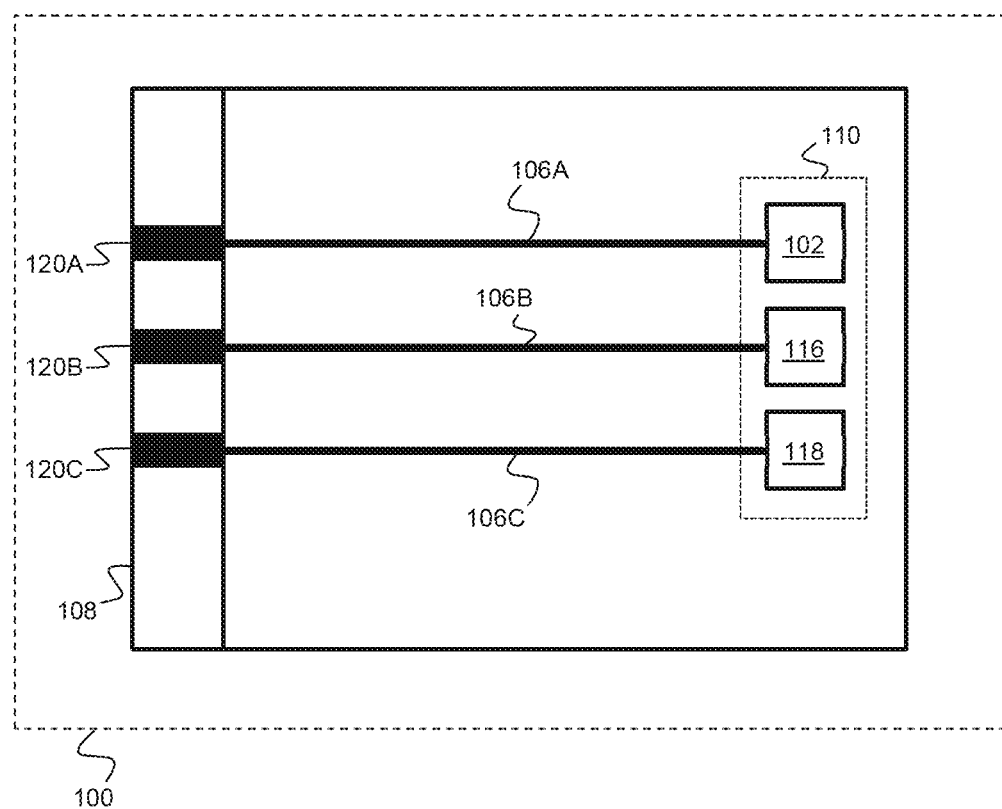

FIG. 2B illustrates an example implementation of a sensor device that includes 100 that includes a modified working electrode 102, a reference electrode 116, a counter electrode 118. The modified working electrode 102, the reference electrode 116 and the counter electrode 118 are provided on the same substrate 108. The substrate 108 can be insulated. It is understood that any of the electrodes of the sensor 100 can be self-supporting and do not need to be provided on the substrate 108. A connection 106a connects the sensing electrode 102 to a contact surface 120a. A connection 106b connects the reference electrode 116 to a contact surface 120b. A connection 106c connects the counter electrode 118 to a contact surface 120c. A common sample receiving region 110 is provided for all of the electrodes 102, 116, 118. It will be appreciated that the sample receiving region does not need to cover the regions defined by the electrodes, in part or in whole, as other configurations for providing the sample to the electrodes 102, 116, 118 can be designed (a microfluidic channel for example). Distinct sample receiving regions can also be provided for each electrode 102, 116, 118.

Example Voltametric Detection Methods Employing Modified Working Electrodes Having Radical-Scavenging Capped Nanozymes In some embodiments, an electrochemical sensor having a modified working electrode according to the present example methods, or variations thereof, may be employed for the detection of an analyte using a voltammetry technique. Voltammetry techniques are electroanalytical techniques based on the detection and quantification of an analyte, by measuring a current as an applied potential is varied. Non-limiting examples of voltametric methods include cyclic voltammetry (CV), linear sweep voltammetry (LSV), differential pulse voltammetry (DPV), and square wave voltammetry (SWV). CV is performed by cycling the potential of a working electrode ramped linearly versus time and measuring the resulting current. LSV measures the current at the working electrodes while the potential between the working electrode and a reference electrode is swept linearly in time. In the DPV technique a potential scan is recovered by imposing potential pulses with a constant amplitude. SVVV is a large-amplitude differential technique in which a waveform composed of a symmetrical square wave, superimposed on a base staircase potential, is applied to the working electrode.

Example Sensor Device

Figure 2C:
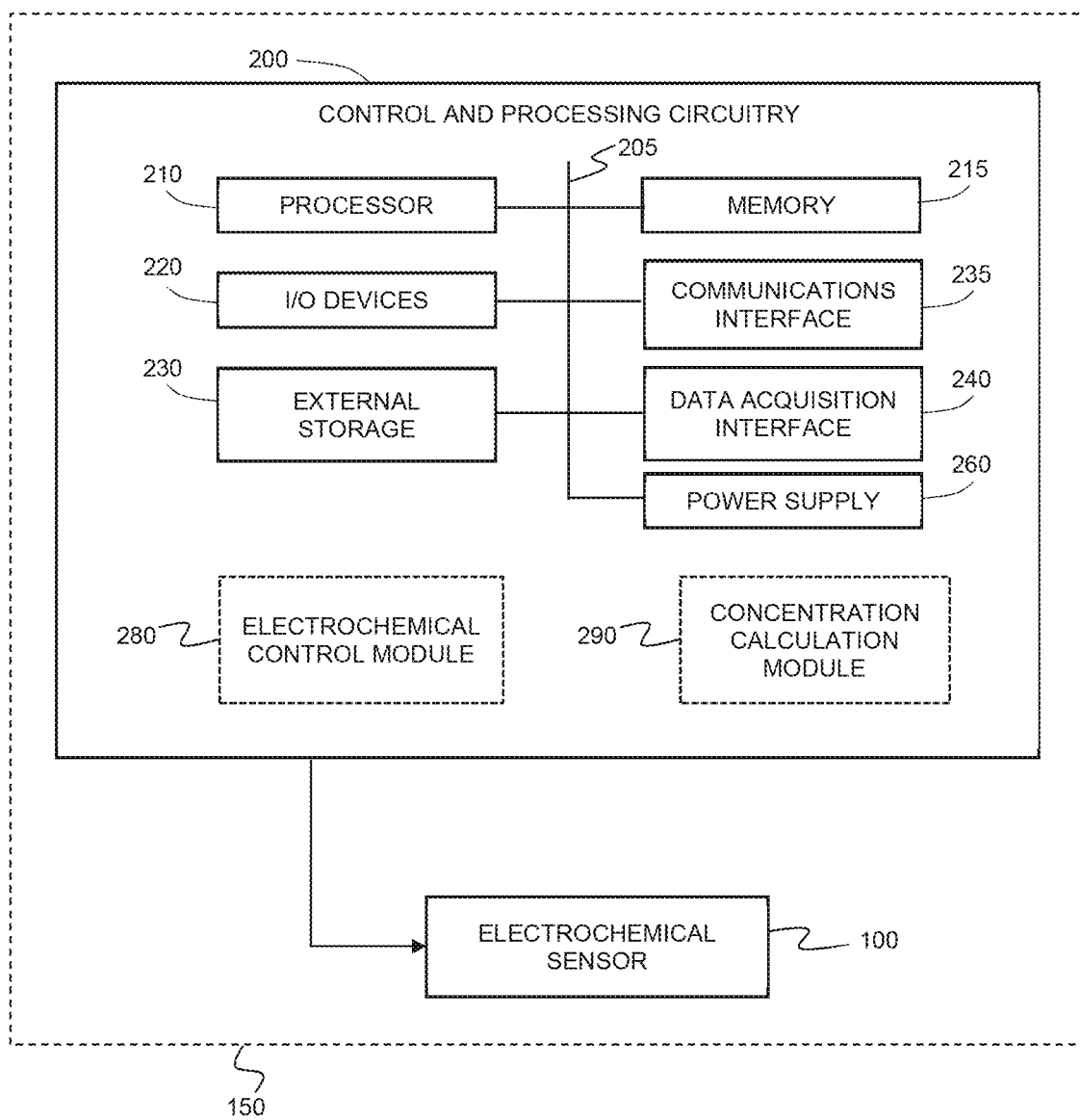
FIG. 2C is an example system for performing electrochemical detection of phenolic analytes using a modified electrode.

Referring now to FIG. 2C, a system for performing electrochemical detection with a sensor having a working electrode modified with radical-scavenging capped nanozymes is schematically illustrated. The example system includes an electrochemical sensor 100, which may include a modified working electrode, a reference electrode, and a counter electrode.

The electrochemical sensor 100 is operatively coupled to control and processing circuity 200. As shown in the example embodiment illustrated in FIG. 2C, the control and processing circuitry 200 may include a processor 210, a memory 215, a system bus 205, one or more input/output devices 220, and a plurality of optional additional devices such as communications interface 235, external storage 230, data acquisition interface 240 and a power supply 160. The example methods described above can be implemented via processor 210 and/or memory 215. As shown in FIG. 2C, executable instructions represented as electrochemical control module 280 and concentration calculation module 290 are processed by control and processing circuitry 200 to execute instructions for performing one or more of the methods described in the present disclosure, or variations thereof. Such executable instructions may be stored, for example, in the memory 215 and/or other internal storage.

The methods described herein can be partially implemented via hardware logic in processor 210 and partially using the instructions stored in memory 215. Some embodiments may be implemented using processor 210 without additional instructions stored in memory 215. Some embodiments are implemented using the instructions stored in memory 215 for execution by one or more microprocessors. Thus, the disclosure is not limited to a specific configuration of hardware and/or software.

It is to be understood that the example system shown in the figure is not intended to be limited to the components that may be employed in a given implementation. For example, the system may include one or more additional processors. Furthermore, one or more components of control and processing circuitry 200 may be provided as an external component that is interfaced to a processing device. Furthermore, although the bus 205 is depicted as a single connection between all of the components, it will be appreciated that the bus 205 may represent one or more circuits, devices or communication channels which link two or more of the components. For example, the bus 205 may include a motherboard. The control and processing circuitry 200 may include many more or less components than those shown. In some example implementations, some aspects of the example methods described herein, such as the processing of the measured signals to calculate one or more blood pressure measures, may be performed via one or more additional computing devices or systems, such as a mobile computing device connected via a local wireless network (such as Wi-Fi or Bluetooth), and/or a remote server connected over a wide area network.

In some example implementations, the electrochemical sensor 100 is provided on a disposable cartridge that can be removably engaged with the control and processing system 200 for performing electrochemical detection. The control and processing circuity may be housed in a portable device.

The electrochemical sensor 100 may be provided according to a wide variety of formats, including, but not limited to, the example open format shown in FIGS. 2A and 2B, a microfluidic device configuration (optionally including one or more valves that are controllable by the control and processing circuitry 200 when the microfluidic device is engaged with the control and processing circuity), and a lateral flow configuration. In some example implementations, the electrochemical sensor may be reusable component that is integrated with the control and processing circuitry, as schematically shown by 150.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine-readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

Methods of Fabrication of Modified Electrodes

In some example implementations involving electrical sensing, an electrode, such as working electrode in the case of an electrochemical testing device, may be modified by the incorporation of radical-scavenging capped nanozymes.

The working electrode that is to be modified by the inclusion of radical-scavenging capped nanozymes may be made from any suitable conductive material. In one embodiment, the working electrode may include a carbon-based material, a nanomaterial, a metal-based material, or a combination thereof. In one embodiment, the electrode may include carbon, gold, platinum, palladium, ruthenium, rhodium, or a combination thereof. In a further example implementation, the electrode may include a screen-printed electrode (SPE). The working electrode may be provided in any suitable shape or size. Examples of SPEs include, but are not limited to, a Zensor electrode, a Dropsens electrode, and a Kanichi electrode.

In some example implementations, a working electrodes may be modified by drop-casting a suspension of synthesized radical-scavenging capped nanozymes onto the electrode surface (for example, a volume of approximately 1-2.5 µL) and subsequently annealing the modified electrode.

In an example implementation involving the incorporation of thiocyanate capped nanomaterials onto an electrode surface, a suspension of thiocyanate capped nanomaterials may be drop cast onto the electrode and annealed at 70-120° C. for 1-5 h inside a hot air oven (BINDER, USA).

The modified sensor can be fabricated using any suitable process capable of associating the radical-scavenging capped nanozymes with the electrode surface. The electrode may be polished and/or washed prior to the deposition of the radical-scavenging capped nanozymes. The electrode may be washed after the deposition of the radical-scavenging capped nanozymes.

The radical-scavenging capped nanozyme suspension that is contacted with the electrode during the deposition process may include an aqueous solvent, an organic solvent, or a mixture thereof.

In one example implementation, the radical-scavenging capped nanozymes can be adhered to electrode via electrodeposition. In embodiments in which electrodeposition is used to associate the radical-scavenging capped nanozymes with the electrode surface, the electrode can receive an electrolytic solution (which can be, without limitation, a buffer, such as, for example a phosphate buffered saline).

In some embodiments, the radical-scavenging capped nanozymes can be adhered to the electrode by the application of applying at least one potential to the electrode. In a specific example implementation, a plurality of potentials (e.g., a potential scan) can be applied to the electrode in contact with the radical-scavenging capped nanozyme suspension. In still another example implementation, a voltammetry technique can be applied to the electrode in contact with the radical-scavenging capped nanozyme suspension to facilitate deposition.

In some example implementations, the entire surface of the electrode (e.g. a working electrode) may be contacted with the radical-scavenging capped nanozyme suspension, while in other example implementations, only a portion of the surface of the electrode may be contacted with the radical-scavenging capped nanozyme suspension. In some example implementations, two or more layers of the radical-scavenging capped nanozymes may be deposited onto the electrode.

Sensitive EtOH Electrochemical Assay Based on Working Electrode Modified by Radical-Scavenging Capped Nanozymes In some example implementations, as shown in further detail in the examples below, embodiments of the present disclosure may be implemented as a rapid EtOH detection device with a sensitivity that is suitable for roadside alcohol testing. The device may include a reader, such as control and processing circuitry 200 in FIG. 2C and a test cartridge that includes an electrochemical sensor, such as electrochemical sensor 100 in FIG. 2C.

In one example implementation, the electrochemical sensor may be provided in a kit that includes a quantity of AOx that is contacted with a sample by an operator to generate $H_2O_2$ from EtOH present within the sample. In some example implementations, the AOx may be provided as a reagent that is stored within a reagent reservoir on the test cartridge, where dispensing of the reagent to contact the sample may be performed manually by the user interacting with the test cartridge, or under actuation of one or more dispensing devices (e.g. valves in fluid connection with a reagent pouch) that are integrated with the test cartridge and actuated automatically by the reader (e.g. via one or more motor actuators integrated with the reader).

In some example implementations, a working electrode of the electrochemical sensor is modified by thiocyanate-capped nanozymes, such as thiocyanate-capped metallic nanoparticles (e.g. gold, silver or copper nanoparticles). The sample, having been contacted with the AOx reagent to generate a solution containing $H_2O_2$, is contacted with the modified working electrode and incubated for a pre-selected time period prior to performing electrochemical read-out of the assay signal.

In some example implementations, the assay signal is read after incubation of the solution containing $H_2O_2$ with the thiocyanate-capped nanoymzes for less than 5 minutes, less than 3 minutes, less than 2 minutes, or less than or equal to 1 minute. The present inventors have found that suitable pH range for the assay may be between 6.5-8.5 and that the characteristic reduction current can be measured at a potential range of 0.3-0.4 V.

When this example EtOH assay is performed according to these conditions, the present inventors have found that EtOH can be detected within a concentration range of approximately of 0.1%~0.02%, which corresponds to the legal limit stipulated in many countries. Accordingly, when implemented in a portable format as an onsite (e.g. roadside) electrochemical test device, the present example EtOH sensor is capable of detecting and quantifying the concentration of EtOH with a high degree of accuracy and with high levels of repeatability and reproducibility, as demonstrated in the following examples.

The following examples are presented to enable those skilled in the art to understand and to practice embodiments of the present disclosure. They should not be considered as a limitation on the scope of the disclosure, but merely as being illustrative and representative thereof.

EXAMPLES

Example 1

Materials and Methods

Materials

Gold (III) chloride trihydrate (HAuCl4. 3H2O), sodium thiocyanate, phosphate buffer, alcohol oxidase (AOx), and 3,3',5,5'-tetramethylbenzidine were purchased from a chemical supplier (Sigma-Aldrich, USA). All the chemicals are of analytical grade and have been used as received without further purification. The screen-printed electrodes used in this study were purchased from Zensors Inc., USA.

Synthesis of Thiocyanate Capped Nanomaterials

An example synthesis method for one-step thiocyanate-capped nanomaterials was developed using sodium thiocyanate (NaSCN) as a reducing as well as a stabilizing agent. A 1-10 mM (1-10 mL) aqueous solution of $HAuCl_4.3H_2O$ was heated to its boiling point at 70-100° C. using a water bath. A quantity of 1-5 mL (1-5 mg/mL) of aqueous sodium thiocyanate solution was added and the heating was continued for approximately 5-30 more minutes. The formation of thiocyanate capped nanomaterials was signaled by the change in the color (reddish pink) of the solution. The synthesized thiocyanate capped nanomaterials (i.e., TC-Au NPs) solution was centrifuged several times at (e.g. at 4,000-15,000 rpm for 10-30 min) and redispersed in ultra-pure water (18 MʊƆ).

Terephthalic Acid (TA) Test

The presence of .OH radicals in reaction media was confirmed through the terephthalic acid test. The .OH radicals formed due to the decomposition of $H_2O_2$ produce a fluorescence signal when contacting terephthalic acid, which allows the correlation of the concentration of $H_2O_2$ and the intensity of fluorescent products with the peroxidase-like activity of TC-Au NPs. A 0.1~0.5 mM (20~200 μL) aqueous solution of terephthalic acid was induced to react with TC-Au NPs (10~50 μL) for 1~10 min at room temperature, in the presence of different concentrations of a $H_2O_2$ solution. Subsequently, the fluorescence intensity of the reaction product was quantified using a fluorescence spectrophotometer (Synergy H1, BioTeK, USA).

Colorimetric Assay of EtOH

Colorimetric EtOH assays were carried out in a PBS buffer (pH 7.4) at 25° C. Initially, a 50 μL solution of AOx (2 units/mL) was prepared in a 48-well plate, after which different concentrated EtOH solutions (50 μL) were added separately and maintained at room temperature for 30 min. A 50 μL TC-Au NPs and 10 μL TMB (10 mM) solutions were added to each well to react with $H_2O_2$ that was enzymatically generated during the reaction of EtOH and AOx. The solution color change at this stage was recorded using UV-Vis spectroscopy.

Modification of Electrodes Surface for Electrochemical EtOH Assay

The working electrodes (on which the reaction of interest is occurring) were modified by drop-casting 5-20 μL of the synthesized thiocyanate capped nanomaterials (e.g. TC-Au NPs) and annealing at 70-120° C. for 1-5 h inside a hot air oven (BINDER, USA). In the present example, three layers of TC-Au NPs were cast to ensure uniform coverage of the electrode surface. All the modified electrodes were thoroughly rinsed with PBS buffer (Sigma-Aldrich, USA) for further experiments. AOx solution (5 μL) was then dropped on the working electrode area and kept at 4° C. before performing electrochemical sensing. Electrochemical measurement (e.g. cyclic voltammetry) (PalmSens4 potentiostat, USA) was employed to analyze the electric property of the modified electrodes to detect EtOH concentration.

Example 2

Experimental Results

Detection of EtOH on Modified Electrodes

After the addition of 10-50 μL PBS (pH range 5-9) into the electrochemical cell with 5-20 μL AOx (2-20 U/mL in PBS buffer) solution, target EtOH (0.1%-0.02%) in PBS buffer and saliva buffer was separately added on different electrodes. 2-10 TMB μL (2-10 mM) was then added onto each electrode. The changes in current with varying EtOH concentration was measured with the potentiostat to help quantify EtOH concentration.

Spectroscopic and Microscopic Study of Thiocyanate Capped Nanomaterials

Figure 3A:
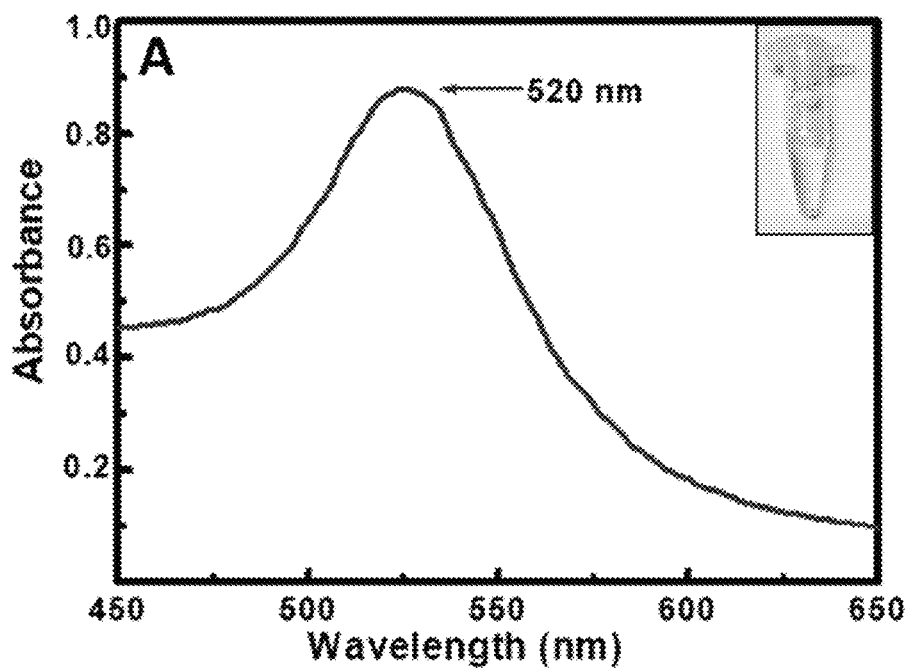
FIGS. 3A and 3B present results from experiments characterizing TC-Au NPs, where FIG. 3A plots the UV-vis spectra of TC-Au NPs (inset: the color of solution)
Figures 3B, 3C:
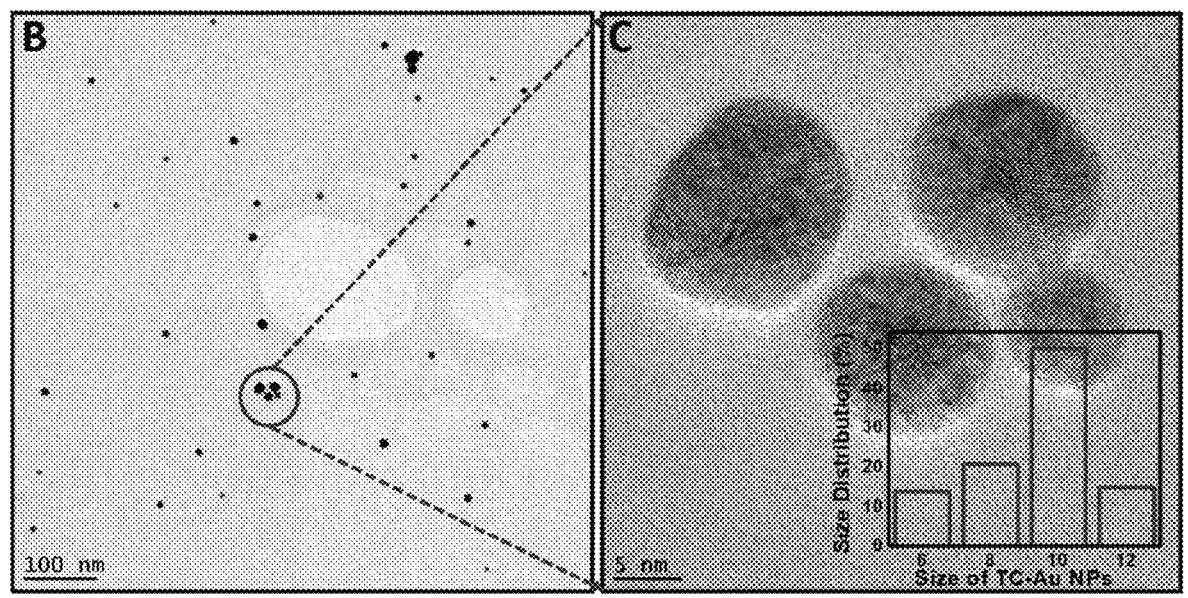
FIG. 3C shows a close view TEM image of TC-Au NPs (inset: the size distribution profile of TC-Au NPs).
Figure 3D:
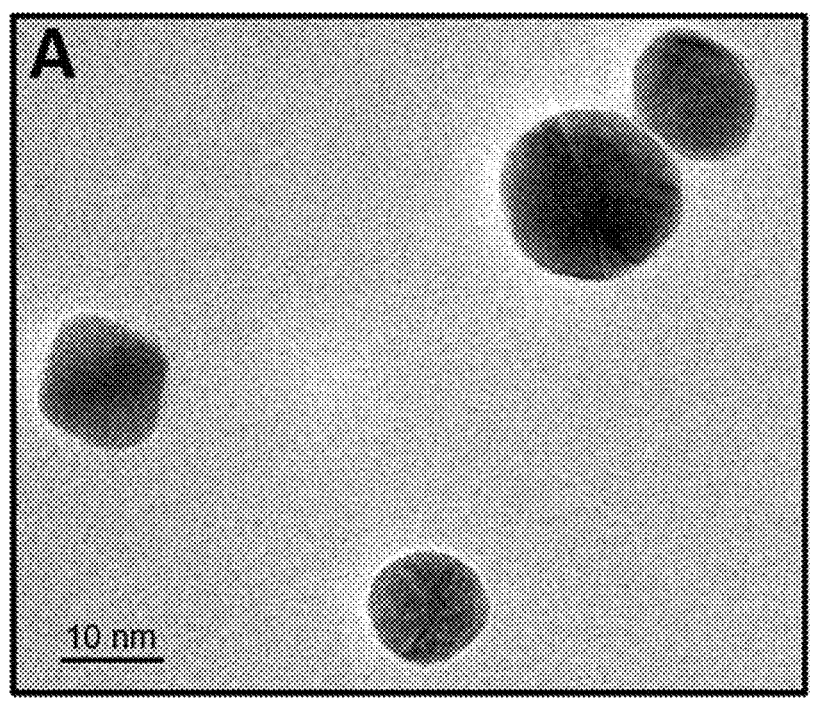
FIGS. 3D and 3E present results from a comparison study of nanozymatic activity, where

The ultraviolet-visible (UV-vis) (Synergy H1, BioTek, USA) spectra of the thiocyanate capped nanomaterials were recorded using a spectrophotometer and are shown in FIG. 3A. The absorbance peak of the TC-Au NP solution is located at 520 nm and the concentration was calculated as 4.7 nM. Furthermore, transmission electron microscopy (TEM) (TECAN, Japan) images revealed TC-Au NP with an average size range of around 3-6 nm, as shown in FIGS. 3B and 3C.

A Comparison Study of Nanozymatic Activity

Figure 3E:
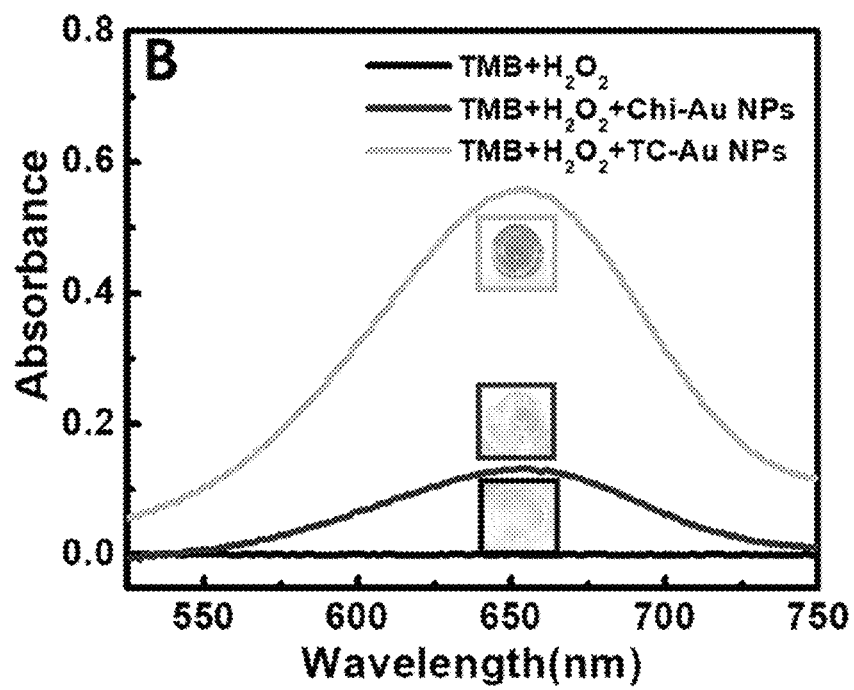

The nanozymatic activity of TC-Au NPs was compared with chitosan capped Au NPs (Chi-Au NPs). As shown in FIG. 3, the TEM image of Chi-Au NPs revealed the size of NPs was around 10 nm (FIG. 3D) and the nanozymatic activity of TC-Au NPs was around 5 times higher than Chi-Au NPs (FIG. 3E). The superior nanozymatic performance of synthesized TC-Au NPs makes it a suitable material to apply in colorimetric biosensor applications.

Optimization of Different Parameters Using Thiocyanate Capped Nanomaterials

Figure 4A:
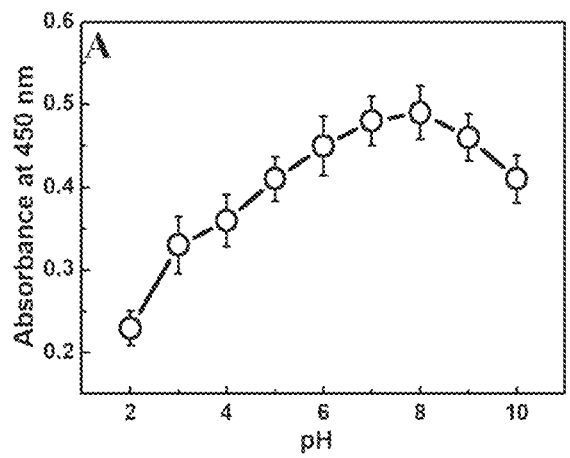
FIGS. 4A-4D are plots that demonstrate the nanozymatic activity of TC-Au NPs at different (FIG. 4A) pH values (reaction conditions: 5 mM TMB and 10 mM $H_2O_2$)
Figure 4B:
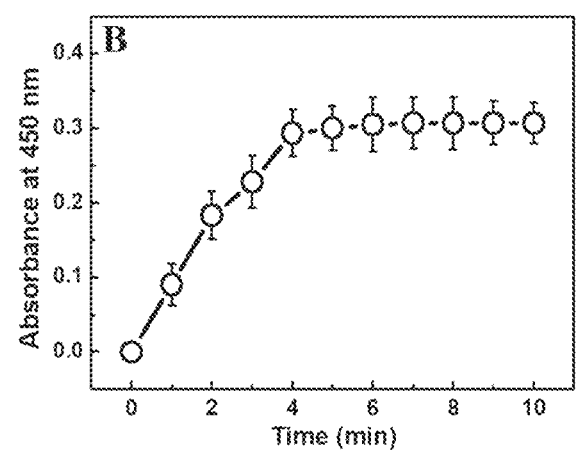
Figure 4C:
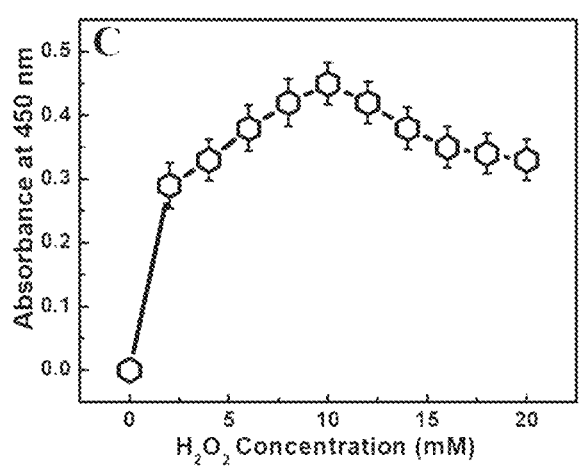
Figure 4D:
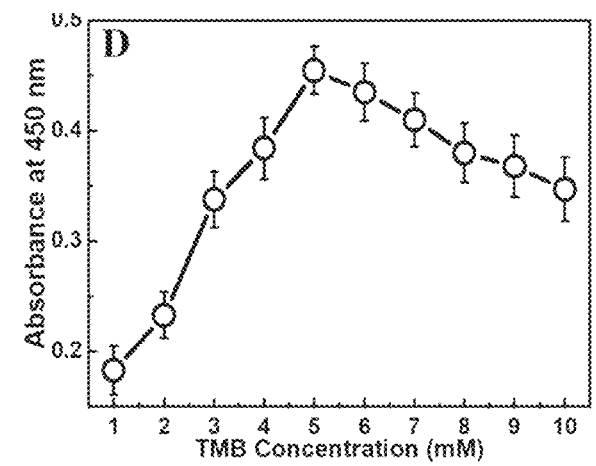

The conditions for optimal catalytic activity of TC-Au NPs were investigated using several parameters, such as pH, temperature, TMB concentration, $H_2O_2$ concentration, and reaction time. These parameters can play a key role in the nanozymatic activity of TC-Au NPs. The investigation was performed by changing the pH value from 2 to 10, the reaction time from 0 to 10 min, the $H_2O_2$ concentration from 0 to 20 mM, and the TMB concentration from 1 to 10 mM. As shown in FIGS. 4A and 4B, a pH 7.5 and a reaction time of 5 minutes were found to provide optimum conditions for nanozymatic activity from TC-Au NPs. Moreover, it was found that an approximately 2:1 ratio of $H_2O_2$ and TMB concentrations was beneficial for obtaining a maximized peroxidase-like activity (FIGS. 4C & 4D).

Catalytic Kinetics of TC-Au NPs

The reaction kinetics of TC-Au NPs were investigated through the apparent steady-state kinetic study. For this, the catalytic performance of TC-Au NPs was examined by changing the concentration of TMB and $H_2O_2$ for 5 min, respectively. The kinetic analysis was carried out by using 50 μL of TC-Au NPs in a reaction volume of 100 μL PBS buffer solution (pH=7.5) with 5 mM TMB or 10 mM $H_2O_2$.

A series of experiments were performed by varying substrate concentration while keeping the concentration of others constant.

Figure 5A:
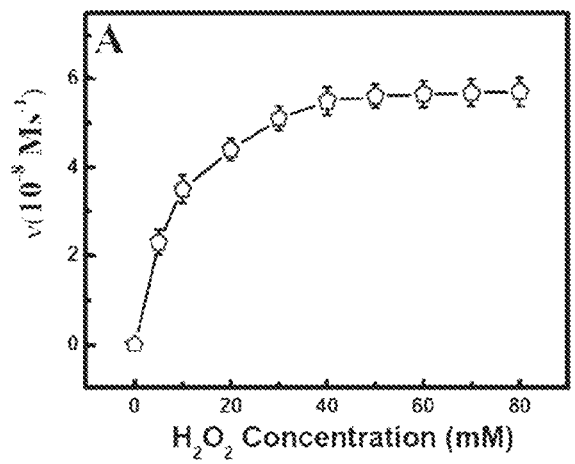
FIGS. 5A-5D plot the steady-state kinetic assay and catalytic characteristics of TC-Au NPs toward various components.
Figure 5B:
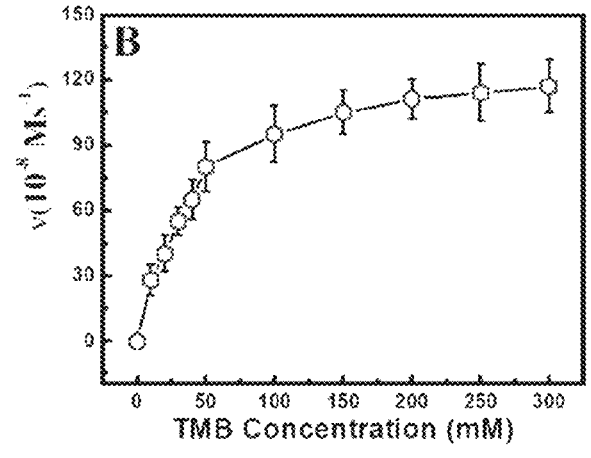

Within a certain range, curves were obtained that satisfied the Michaelis-Menten equation (equation 1) for nanohybrids with both TMB and $H_2O_2$ substrates:

$$V_0 = \frac{V_{max} \cdot [S]}{K_m + [S]}, \quad (1)$$

where $V_0$ is the initial reaction rate, $V_{max}$ is the maximum reaction rate, [S] is the substrate concentration, and $K_m$ is the Michaelis-Menten constant. The resulting parameters are plotted in FIGS. 5A and 5B for both substrates.

Figure 5C:
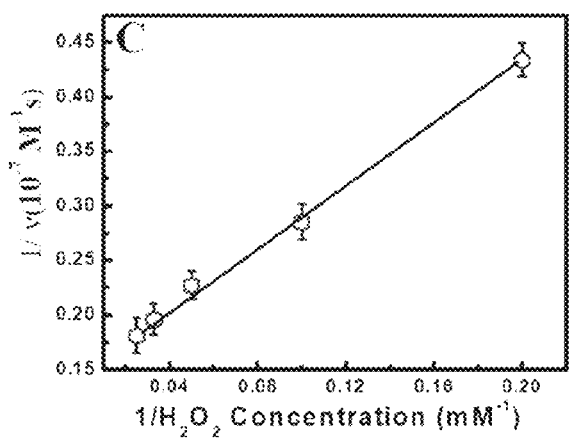
Figure 5D:
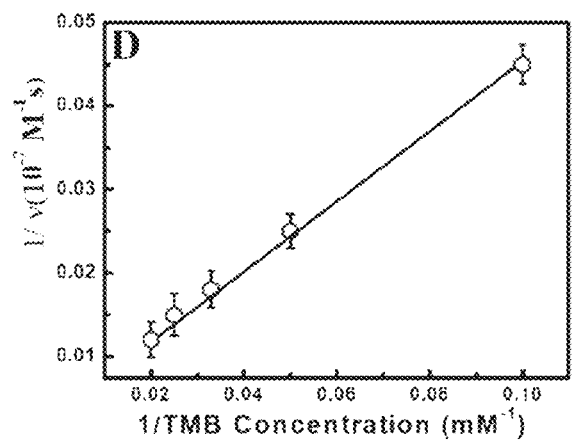

To further analyze the basic kinetic parameters, a Lineweaver-Burk double reciprocal plot was used. The reciprocal of the initial rate was proportional to the reciprocal of the substrate (equation 2) concentration, which was fitted to the double reciprocal of the Michaelis-Menten equation, $$\frac{1}{V} = \frac{K_m}{V_{max}} \cdot \frac{1}{[S]} + \frac{1}{V_{max}} \quad (2)$$

where V, $K_m$, $v_{max}$ and [S] denote the initial rate, the Michaelis-Menten constant, the maximum reaction rate, and the substrate concentration, respectively. The results of this fitting are shown in FIGS. 5C and 5D.

A comparison study of kinetic parameters of TC-Au NPs in was also performed with horseradish peroxidase (HRP) for the oxidation of TMB in the presence of $H_2O_2$. As-synthesized TC-Au NPs showed a lower value of $K_m$ (~0.11 mM) and a higher value of $K_{cat}$ (~2.29×10$^4$ s$^{-1}$) in comparison to HRP ($K_m$ and $K_{cat}$ is 0.434 mM and 4.00×10$^3$ s$^{-1}$ respectively), indicating that the TC-Au NPs had a higher affinity toward TMB than HRP.

The $K_m$ value of TC-Au NPs was higher than that of HRP (3.7 mM) toward $H_2O_2$ (343.04 mM), indicating that the TC-Au NPs had a lower affinity toward $H_2O_2$ than HRP. These results revealed that TC-Au NPs possessed relatively high peroxidase-like activity. The high peroxidase-like activity of TC-Au NPs is expected to be beneficial for the realization of ultrasensitive biosensor.

Nanozymatic Activity of Thiocyanate Capped Nanomaterials

Figure 6:
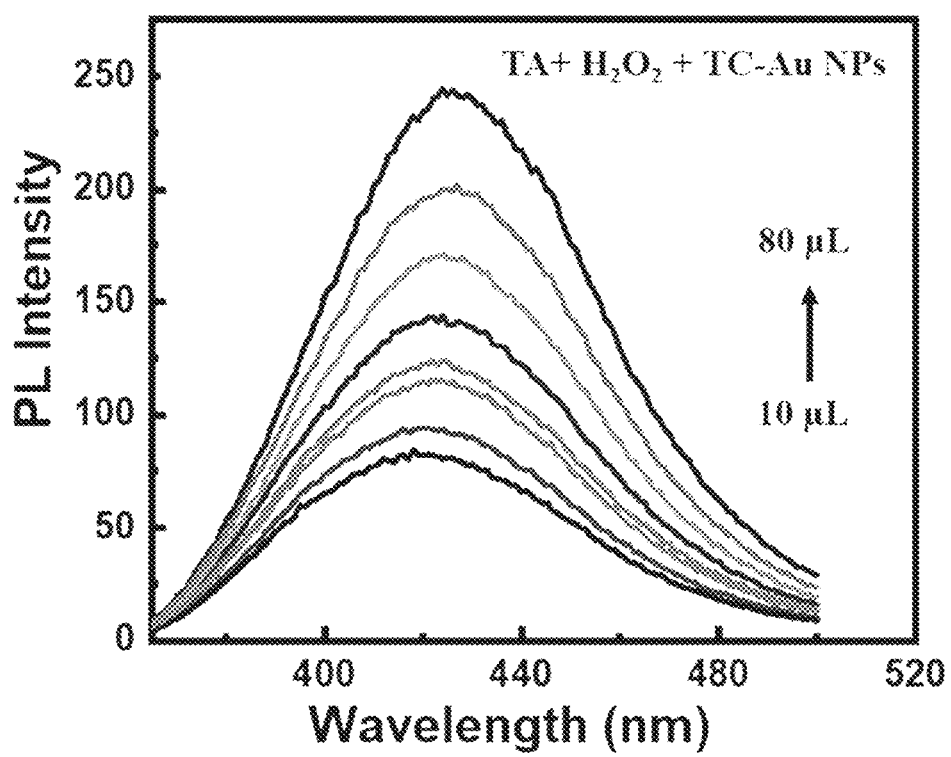
FIG. 6 plots results from a nanozymatic activity study of TC-Au NPs, showing results from a TA based test of hydroxyl radical's formation by TC-Au NPs.
Figure 7:
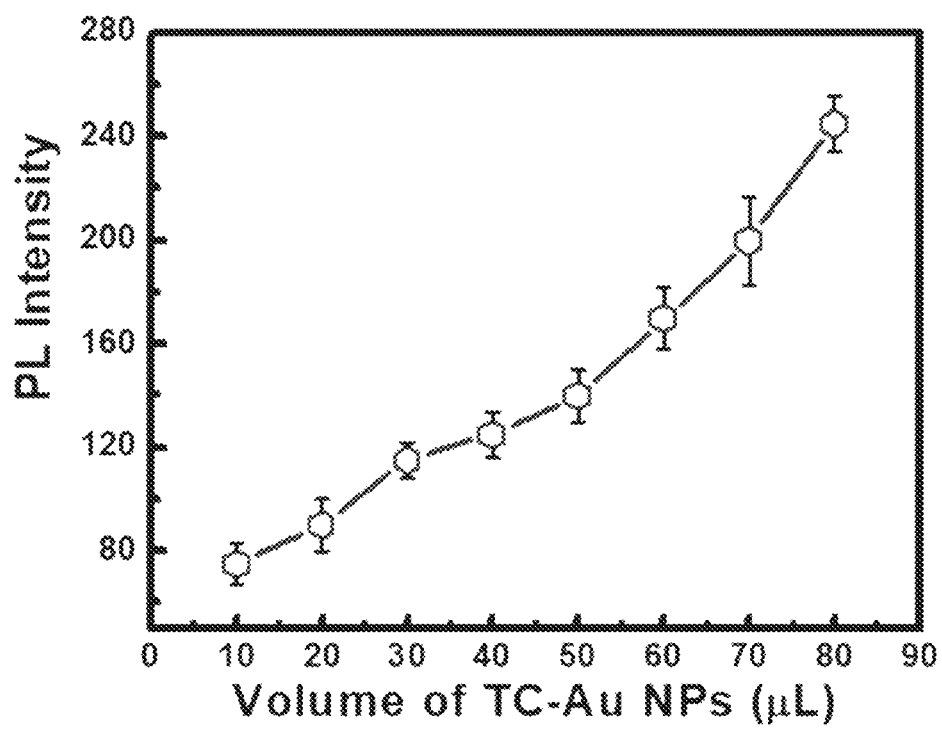
FIG. 7 plots results from a nanozymatic activity study of TC-Au NPs, showing a calibration curve of PL intensity vs different volume of TC-Au NPs.

To confirm the TC-Au NPs assisted decomposition of $H_2O_2$, and the formation of .OH radicals, terephthalic acid (TA) test was performed. It is well-established that a fluorescence signal (fluorescent product of 2-hydroxy terephthalic acid) will appear if .OH radicals form and react with terephthalic acid. In the present example, the fluorescence signal was recorded using a fluorescence spectrophotometer (Synergy H1, BioTeK, USA). As shown in FIG. 6, fluorescence spectra of 2-hydroxy terephthalic acid appear with a peak position located at 428 nm due to the formation of .OH radicals. Moreover, the signal intensity of fluorescence spectra increased with the increasing volume of TC-Au NPs, a good indicator that TC-Au NPs perform the main role in .OH radicals formation (FIG. 7).

Colorimetric Detection of EtOH Via Thiocyanate Capped Gold Nanoparticles

Figure 8A:
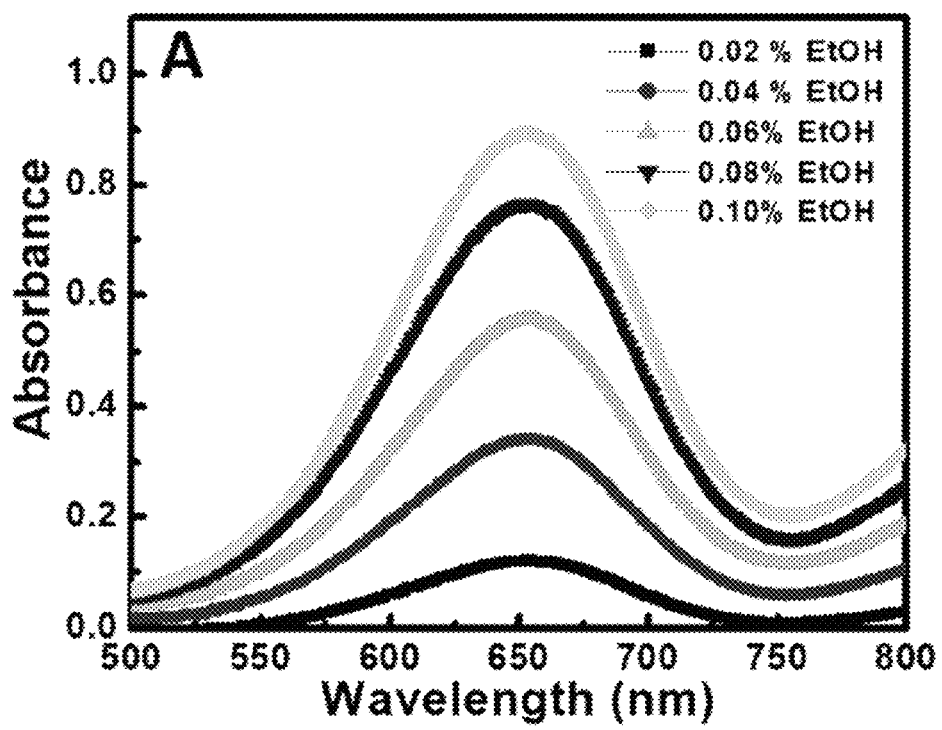
FIGS. 8A and 8B demonstrate the colorimetric detection of EtOH, where FIG. 8A plots UV-Visible spectra of the colored solution with different concentrated EtOH solution and FIG. 8B plots the calibration curve of absorbance peak vs EtOH solution.

The superior kinetic nature and .OH radical forming capability of TC-Au NPs were applied for the colorimetric detection of EtOH. As shown in FIG. 8A, the absorbance of the blue-colored solution in the system of TC-Au NPs/AOx/EtOH/TMB has a peak value at approximately 655 nm. The peak intensity was directly proportional to the increasing concentration of EtOH in reaction, suggesting the higher oxidation of TMB. The present inventors believe that the reason behind the increase in absorbance at 655 nm is the intrinsic peroxidase activity and high .OH radicals forming capability of TC-Au NPs.

Figure 8B:
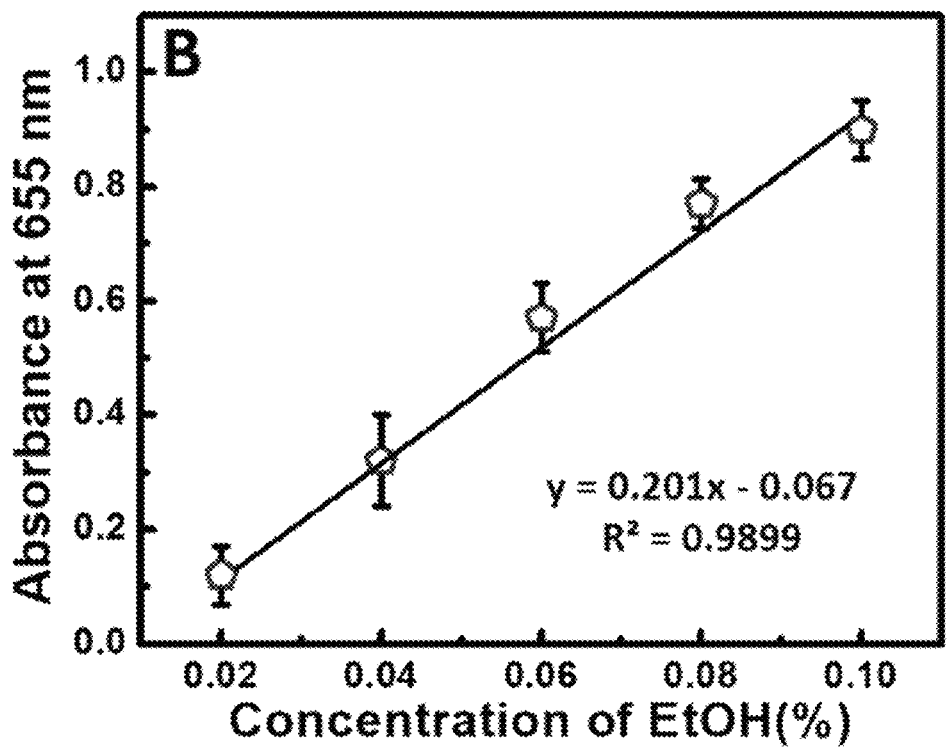

The observed colorimetric changes were found to be correlated with EtOH concentration in the range of 0.1%-0.02%, as can be seen in FIG. 8B. However, the present nanozyme-based colorimetric detection assay was found to require 10-30 min to obtain high sensitivity. Faster assay times can be achieved using an electrochemical approach, as shown below.

Figure 9:
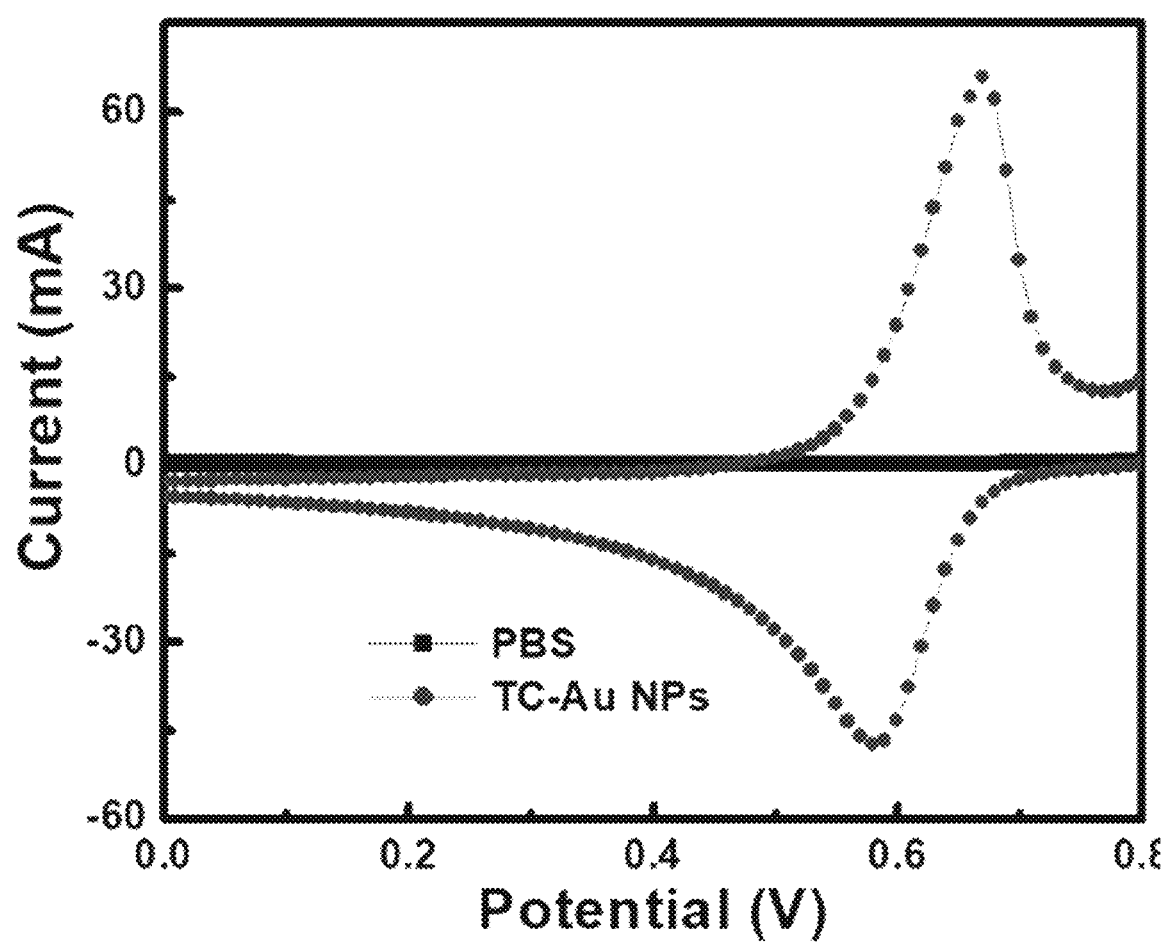
FIG. 9 plots electrochemical responses of TC-Au NPs.

Electrochemical Detection of EtOH Via Thiocyanate Capped Gold Nanoparticles Via Electrochemical Detection of Oxidized TMB Cyclic voltammetry (CV) analysis of the TC-Au NPs/AOx/EtOH/TMB system was performed in PBS media (pH 7.5) to investigate the electric response (current) with different concentrations of EtOH. The electrical responses of an TC-Au NPs modified electrode were initially measured and revealed an oxidation and reduction current located at 0.67 V and 0.58V, respectively. Moreover, modified TC-Au NPs showed enhanced electric signal when compared to the bare electrode and proved a suitable candidate for the electrochemical detection system, as shown in FIG. 9.

Figure 10A:
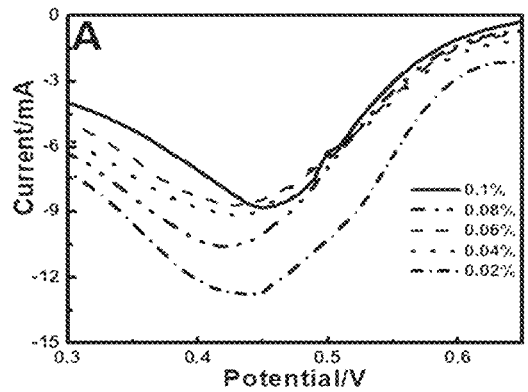
FIGS. 10A-10F plots results from an electrochemical study of analytical performance.
Figure 10B:
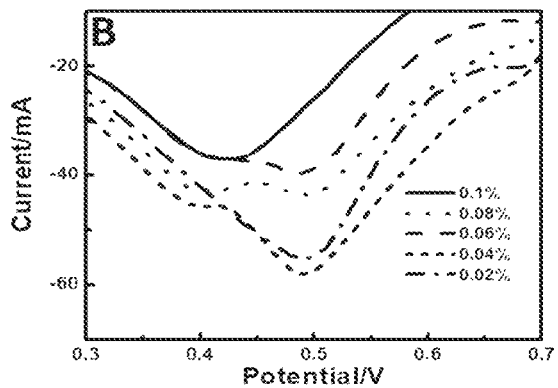

The performance of the sensors was then assessed by monitoring the change in electrochemical current due to the reduction of TMB when a EtOH-containing sample was added. A ramped voltage from −1 v to 1 v was applied at a scan rate of 10-100 mV/S. A significant reduction current was observed at a potential range of 0.3-0.6 V with the reaction time of 1 min, as shown in FIG. 10A. However, the results were not found to be strongly correlated with EtOH concentration. Similar results were observed with the reaction time of 2 min, as shown in FIG. 10B.

Figure 10C:
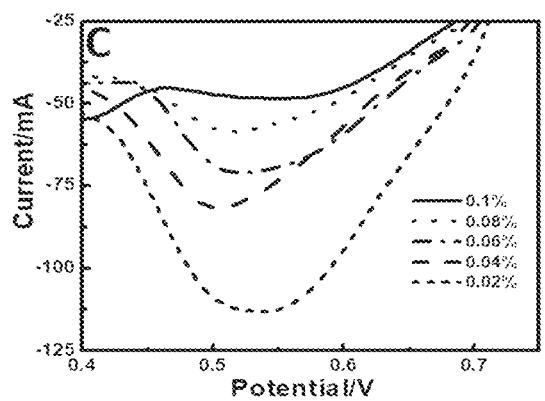
Figure 10D:
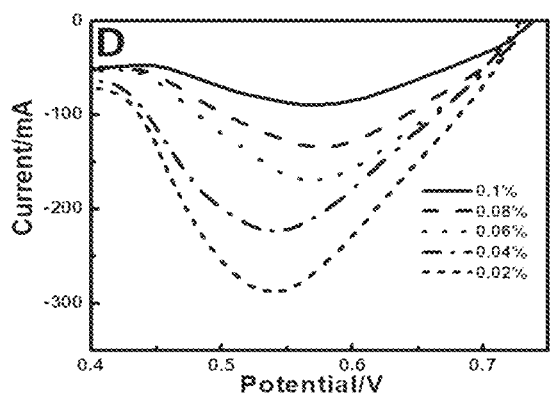
Figure 10E:
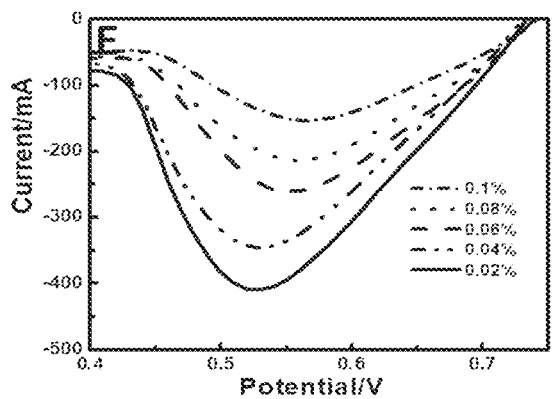

The present inventors found that electrical current responses that were well correlated with EtOH concentrations were observed after 3 minutes of reaction time, with a resulting detection range of EtOH from 0.02-0.1%, as shown in FIG. 10C. Similar results were observed with the reaction time of 4 minutes and 5 minutes, as shown in FIGS. 10D and 10E, which revealed that in the present example, a reaction time of at least 3 minutes was beneficial in establishing a strong correlation between assay signal and EtOH concentration over the tested EtOH concentration range.

Figure 10F:
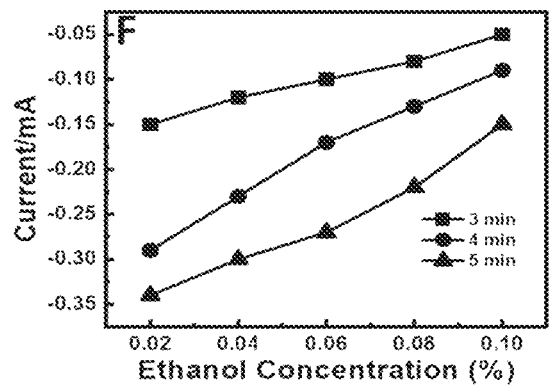

Calibration curves relating measured current to EtOH concentration were constructed for various assay times, as shown in FIG. 10F. These curves demonstrate that the present example ethanol sending method is highly sensitive to the measured EtOH concentration within the range of 0.02-0.1% for assay times beyond 3 minutes.

Electrochemical Detection of EtOH Via Thiocyanate Capped Gold Nanoparticles Via Electrochemical Detection of Reduced $H_2O_2$ In order to develop an electrochemical EtOH assay with a shorter time to result than the aforementioned detection times of 3 minutes for TMB-based electrochemical detection, an alternative electrochemical detection approach was employed that was based on direct detection of the electrochemical reduction current of $H_2O_2$ was investigated.

Figure 11A:
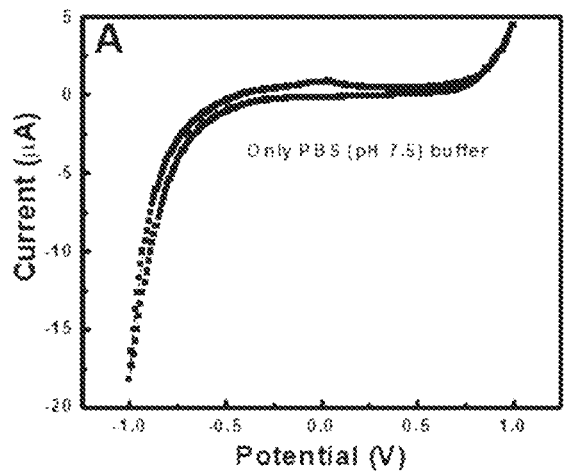
FIGS. 11A-11D plot results from an electrochemical study of TC-Au NPs performance.
Figure 11B:
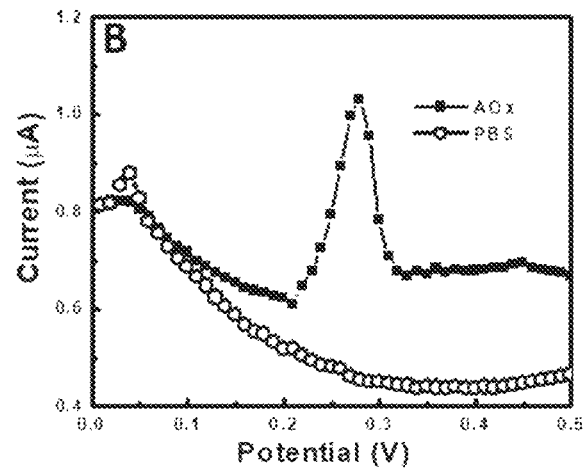
Figure 11C:
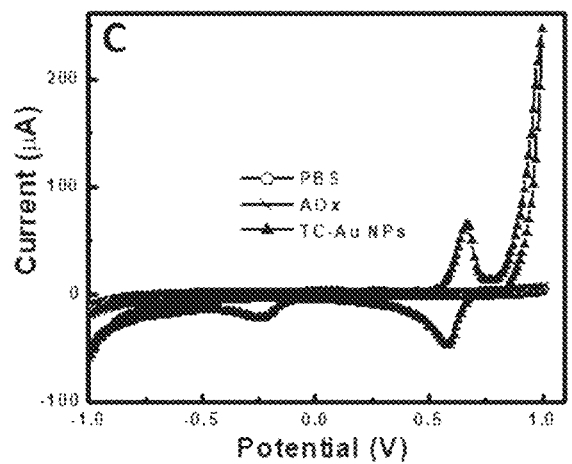
Figure 11D:
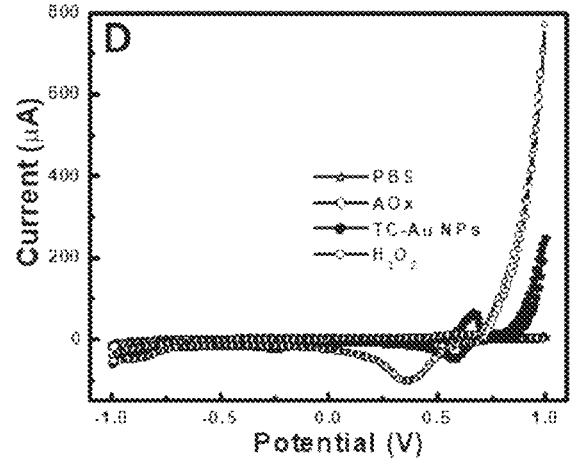

Control experiments were initially performed to determine a suitable reduction potential for $H_2O_2$ sensing. As shown in FIG. 11A, the bare PBS buffer showed no peak in the CV curve. However, after AOx was added, a new peak appeared at 0.28 V due to the oxidation of AOx, as shown in FIG. 11B. After TC-Au NPs were added to this solution, oxidation and reduction peaks were observed at 0.62 and 0.58 V, respectively, as shown in FIG. 11C. After adding $H_2O_2$, distinct reduction peak was observed at 0.38 V, thereby identifying a unique target potential for EtOH detection, as shown in FIG. 11D.

Figure 12A:
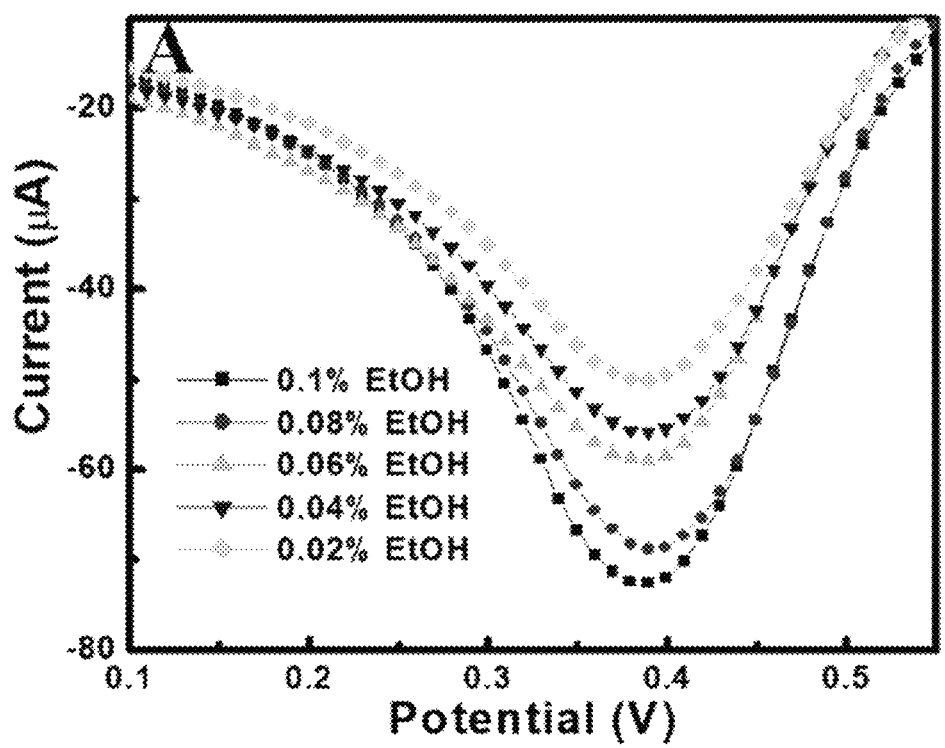
FIGS. 12A and 12B demonstrate the electrochemical analytical performance of EtOH using second approach involving the detection of the reduction current of $H_2O_2$, where FIG. 12A plots the CV of EtOH detection using reduction current of $H_2O_2$ within 1 min, and FIG. 12B plots the calibration curve of current versus EtOH at different concentration.
Figure 12B:
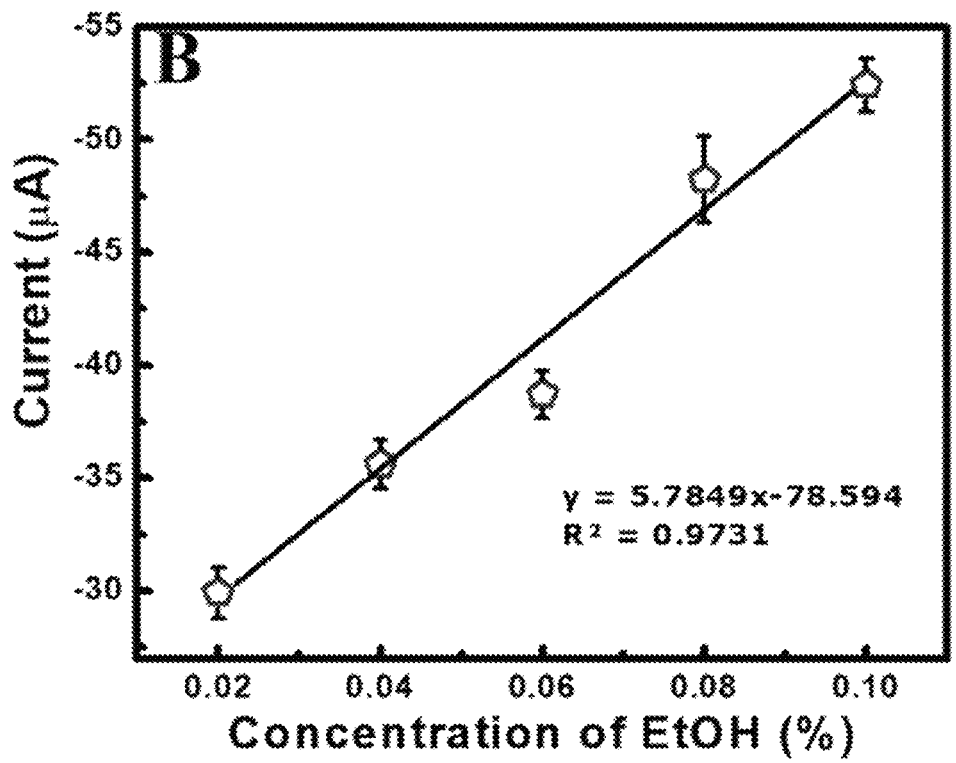

The dependence of the reduction current on varying concentrations of EtOH was subsequently investigated. As shown in FIG. 12A, a clear dependence of reduction current on EtOH concentration was observed within the detection range of 0.02-0.1% based on a reaction readout time of only one minute. A calibration curve of current versus EtOH concentration was also constructed over this concentration range, demonstrating the linear relationship between the current and EtOH concentration, as shown in FIG. 12B.

Figure 13A:
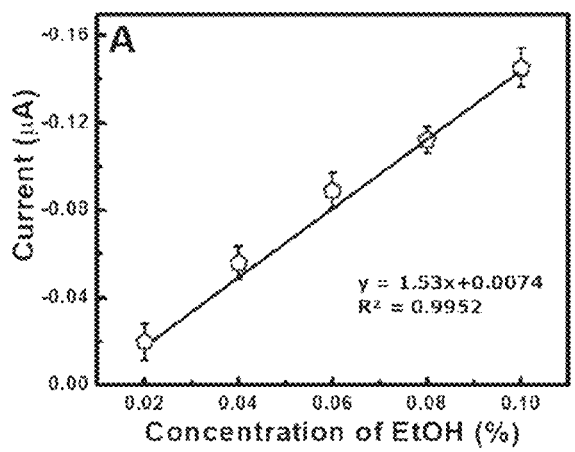
FIGS. 13A-13D plot results demonstrating the electrochemical detection of EtOH in simulated saliva (FIG. 13A and FIG. 13C) and in real-saliva samples (FIG. 13B and FIG. 13D).
Figure 13B:
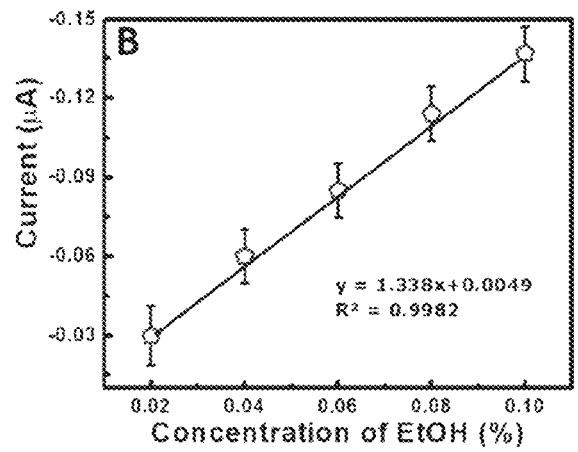
Figure 13C:
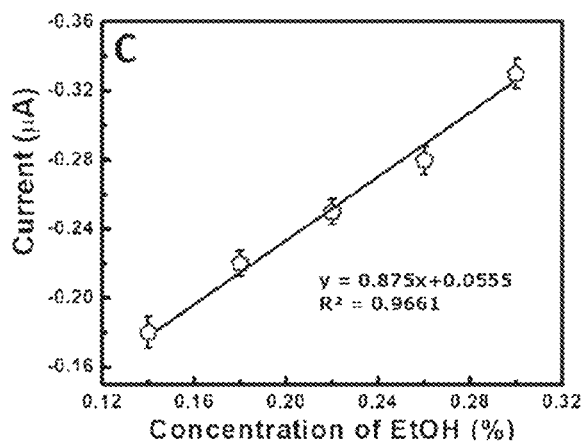
Figure 13D:
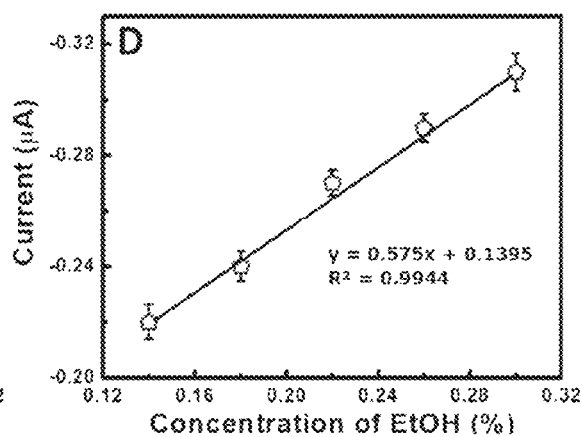

After confirming the reduction voltage of $H_2O_2$ through CV analysis, square-wave voltammetry (SWV) was applied in the proposed detection strategy. SWV detection was performed in simulated saliva and real-saliva samples that were collected from a healthy person. As shown in FIGS. 13A and 13C, the relation between EtOH concentration and changes of current was linear within the range of 0.02-0.3% in a simulated saliva sample. A similar result was achieved in the real saliva sample FIGS. 13B and 13D; however, the current decreased marginally due to the higher viscosity of the real-saliva sample. The limit of detection was determined to be 0.013%, as calculated based on the standard deviation method.

Potential interferences in the EtOH assay in using the proposed $H_2O_2$ reduction current strategy were also investigated. As shown in FIG. 14A, the current at 0.38V was very high with target EtOH (0.02%), whereas the current was very negligible for ascorbic acid (0.01 mM), sucrose (0.01 mM), fructose (0.01 mM), phosphoric acid (0.01 mM), methanol (0.02%), uric acid (0.01 mM), and isopropanol (0.02%). Those results reveled that the present study was very specific to target EtOH.

Assay Validation Based on EtOH Measurement in Diluted Commercial Beer

Figures 14, 15:
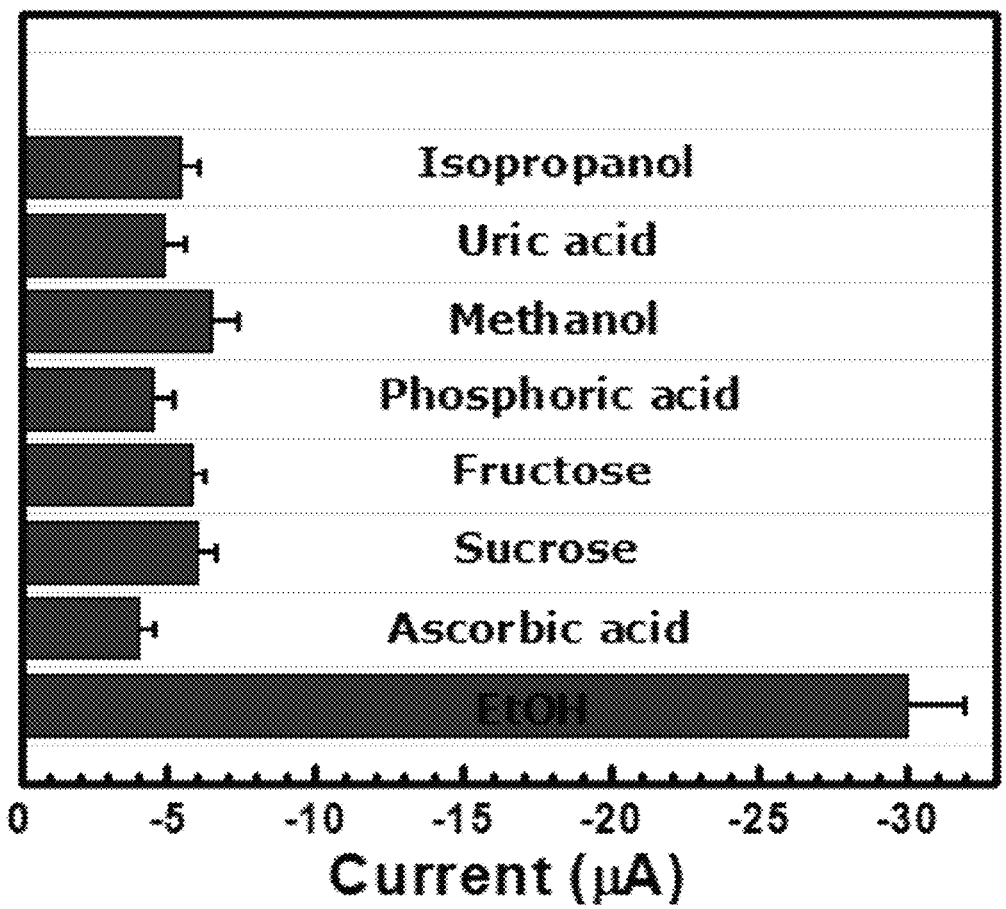
FIG. 14 plots the measured electrocurrent arising from various interferents, demonstrating the selectivity of example EtOH assay.
FIG. 15 is a table presenting results from precision (relative standard deviation, RSD %) and recovery studies of the example EtOH assay.

In order to validate the performance of the preceding example embodiment involving the direct electrochemical detection of a reduction current associated with the decomposition of $H_2O_2$, the recovery of ETOH in commercial beer samples were evaluated. The beer samples were diluted at four different concentrations (0.02, 0.06, 0.14, and 0.20%). As shown in FIG. 15, the recovery of EtOH by the proposed assay was in the range of 93.3-112.9% with the relative standard deviation (RSD) of less than 3%. These results confirm the reliability and high accuracy of the proposed strategy and provide great potential for sensitive, specific, and convenient detection of EtOH in real samples.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of performing an assay to detect an assay signal associated with a presence of hydrogen peroxide, the method comprising:
    contacting a solution containing hydrogen peroxide with a capped peroxidase-mimetic nanozyme, the capped peroxidase-mimetic nanozyme comprising a radical-scavenging capping ligand;
    incubating the solution with the capped peroxidase-mimetic nanozyme such that decomposition of the hydrogen peroxide is catalyzed by the capped peroxidase-mimetic nanozyme, wherein the radical capping agent facilitates the capture and retention of one or more radicals for enhancing a catalytic reaction compared to an uncapped peroxidase-mimetic nanozyme; and
    detecting the assay signal associated with the decomposition of the hydrogen peroxide.

2. The method according to claim 1 wherein the radical-scavenging capping ligand comprises thiocyanate.

3. The method according to claim 1 wherein the radical-scavenging capping ligand comprises a thiol group.

4. The method according to claim 1 wherein the radical-scavenging capping ligand comprises tannic acid.

5. The method according to claim 1 wherein the capped peroxidase-mimetic nanozyme comprises a metallic nanoparticle capped with the radical-scavenging capping ligand.

6. The method according to claim 5 wherein the metallic nanoparticle is selected from the group consisting of gold nanoparticles, silver nanoparticles and copper nanoparticles.

7. The method according to claim 1 wherein the solution containing hydrogen peroxide is obtained by contacting an ethanol solution with alcohol oxidase.

8. The method according to claim 7 wherein the assay signal is processed to infer a concentration of ethanol in the ethanol solution.

9. The method according to claim 1 further comprising adding a substrate to the solution, the substrate being selected to exhibit a color change upon oxidation of the substrate by the hydrogen peroxide in the presence of the capped peroxidase-mimetic nanozyme;
    wherein the assay signal is a colorimetric assay signal.

10. The method according to claim 9 wherein the substrate is 3,3',5,5'-tetramethylbenzidine.

11. The method according to claim 1 wherein the capped peroxidase-mimetic nanozyme resides on an electrode and wherein the assay signal is a voltametric assay signal.

12. The method according to claim 11 wherein the voltametric assay signal is associated with the reduction of the hydrogen peroxide by the electrode, the reduction being catalyzed by the capped peroxidase-mimetic nanozyme.

13. The method according to claim 11 further comprising adding a substrate to the solution, the substrate being oxidizable by the hydrogen peroxide in the presence of the capped peroxidase-mimetic nanozyme;
    wherein the assay signal is a reduction current associated with reduction of the oxidized substrate by the electrode.

14. The method according to claim 2 wherein the solution containing hydrogen peroxide is obtained by contacting an ethanol solution with alcohol oxidase, and wherein the assay signal is processed to infer a concentration of ethanol in the ethanol solution.

15. The method according to claim 14 further comprising adding a substrate to the solution, the substrate being selected to exhibit a color change upon oxidation of the substrate by the hydrogen peroxide in the presence of the capped peroxidase-mimetic nanozyme;
    wherein the assay signal is a colorimetric assay signal.

16. The method according to claim 15 wherein the substrate is 3,3',5,5'-tetramethylbenzidine.

17. The method according to claim 14 wherein the capped peroxidasemimetic nanozyme resides on an electrode and wherein the assay signal is a voltametric assay signal.

18. The method according to claim 17 wherein the voltametric assay signal is associated with the reduction of the hydrogen peroxide by the electrode, the reduction being catalyzed by the capped peroxidase-mimetic nanozyme.

19. The method according to claim 17 wherein the solution is incubated for less than 5 minutes before reading the assay signal.

20. The method according to claim 17 wherein the solution is incubated for less than 3 minutes before reading the assay signal.

21. The method according to claim 17 wherein the solution is incubated for less than 2 minutes before reading the assay signal.

22. The method according to claim 17 wherein the solution is incubated for less than or equal to 1 minute before reading the assay signal.

23. The method according to claim 14 wherein the concentration of ethanol inferred from the assay signal is between 0.1% and 0.02%.

24. The method according to claim 17 further comprising adding a substrate to the solution, the substrate being oxidizable by the hydrogen peroxide in the presence of the capped peroxidase-mimetic nanozyme;

wherein the assay signal is a reduction current associated with reduction of the oxidized substrate by the electrode.

25. The method according to claim 24 wherein the substrate is 3,3',5,5'-tetramethylbenzidine.

26. An electrochemical sensor for detecting a presence of ethanol in a sample, the electrochemical sensor comprising a working electrode modified with a capped peroxidase-mimetic nanozyme, wherein said capped peroxidase-mimetic nanozyme comprises a radical-scavenging capping ligand which facilitates the capture and retention of one or more radicals for enhancing a catalytic reaction compared to an uncapped peroxidase-mimetic nanozyme.

27. The electrochemical sensor according to claim 26 further comprising control and processing circuitry operatively coupled to said working electrode, said control and processing circuitry comprising at least one processor and associated memory, said memory being programmed with instructions executable by said at least one processor for performing operations comprising:

performing a voltametric scan to obtain an assay signal associated with reduction of a hydrogen peroxide at said working electrode, the reduction being catalyzed by said capped peroxidase-mimetic nanozyme; and processing the assay signal to infer a concentration of ethanol in according to calibration data stored in said memory.

* * * * *